United States Patent
Alvarez et al.

(10) Patent No.: US 11,810,644 B2
(45) Date of Patent: Nov. 7, 2023

(54) SYSTEM AND METHOD FOR GENOMIC ASSOCIATION

(71) Applicant: Avalo, Inc., Durham, NC (US)

(72) Inventors: Mariano Alvarez, Durham, NC (US); Cynthia Rudin, Durham, NC (US)

(73) Assignee: Avalo, Inc., Durham, NC (US)

( * ) Notice: Subject to any disclaimer, the term of this patent is extended or adjusted under 35 U.S.C. 154(b) by 0 days.

(21) Appl. No.: 18/119,030

(22) Filed: Mar. 8, 2023

(65) Prior Publication Data

US 2023/0290437 A1 Sep. 14, 2023

Related U.S. Application Data

(60) Provisional application No. 63/350,328, filed on Jun. 8, 2022, provisional application No. 63/350,326, filed on Jun. 8, 2022, provisional application No. 63/325,831, filed on Mar. 31, 2022, provisional application No. 63/317,656, filed on Mar. 8, 2022.

(51) Int. Cl.
| | |
|---|---|
| *G01N 33/48* | (2006.01) |
| *G01N 33/50* | (2006.01) |
| *G16B 20/00* | (2019.01) |
| *G06N 20/00* | (2019.01) |
| *G16B 40/20* | (2019.01) |

(52) U.S. Cl.
CPC .............. *G16B 20/00* (2019.02); *G06N 20/00* (2019.01); *G16B 40/20* (2019.02)

(58) Field of Classification Search
CPC ......... G16B 20/00; G16B 40/20; G06N 20/00
See application file for complete search history.

(56) References Cited

U.S. PATENT DOCUMENTS

| | | | |
|---|---|---|---|
| 2020/0197500 A1 | 6/2020 | Blair et al. | |
| 2021/0142904 A1* | 5/2021 | Michuda | G16H 50/20 |
| 2021/0383892 A1* | 12/2021 | Holzer | G16H 10/60 |

FOREIGN PATENT DOCUMENTS

| | | |
|---|---|---|
| WO | 2010132731 A9 | 10/2011 |
| WO | 2015066564 A1 | 5/2015 |
| WO | 2020181240 A1 | 9/2020 |
| WO | 2020185725 A1 | 9/2020 |

OTHER PUBLICATIONS

Craig et al. Ordering of cosmid clones covering the Herpes simplex virus type I (HSV-I) genome: a test case for fingerprinting by hybridisation. Nucleic Acids Research, vol. 18, pp. 2653-2660. (Year: 1990).*
Barber, Rina Foygel, et al., "Controlling the False Discovery Rate via Knockoffs", The Annals of Statistics 2015, vol. 43, No. 5, 2055-2085 DOI: 10.1214/15-AOS1337 ® Institute of Mathematical Statistics, 2015.
Fisher, Aaron , et al., "All Models are Wrong, but Many are Useful: Learning a Variable's Importance by Studying an Entire Class of Prediction Models Simultaneously", Journal of Machine Learning Research 20 (2019) 1-81 Submitted Nov. 2018; Revised Aug. 2019; Published Dec. 2019.
He, Zihuai , et al., "Genome-wide analysis of common and rare variants via multiple knockoffs at biobank scale, with an application to Alzheimer disease genetics", The American Journal of Human Genetics 108, 2336-2353, Dec. 2, 2021.
He, Zihuai , et al., "Summary statistics knockoff inference empowers identification of putative causal variants in genome-wide association studies", bioRxiv preprint doi: https://doi.org/10.1101/2021.12.06.471440; this version posted Dec. 7, 2021.
Lu, Yang Young, et al., "DeepPINK: reproducible feature selection in deep neural networks", 32nd Conference on Neural Information Processing Systems (NeurIPS 2018), Montréal, Canada.
Sesia, Matteo , et al., "False discovery rate control in genome-wide association studies with population structure", PNAS 2021 vol. 118 No. 40 e2105841118, https://doi.org/10.1073/pnas.2105841118.
Sesia, M. , et al., "Gene hunting with hidden Markov model knockoffs", Biometrika (2019), 106, 1, pp. 1-18, doi: 10.1093/biomet/asy033, Printed in Great Britain, Advance Access publication Aug. 4, 2018.
Sesia, Matteo , et al., "Multi-resolution localization of causal variants across the genome", Nature Communications I (2020)11:1093 I https://doi.org/10.1038/s41467-020-14791-2 I www.nature.com/naturecommunications.
Zhu, Zifan , et al., "DeepLINK: Deep learning inference using knockoffs with applications to genomics", PNAS 2021 vol. 118 No. 36 e2104683118, https://doi.org/10.1073/pnas.2104683118.
Mitterroecker, Philipp , et al., "Multivariate Analysis of Genotype-Phenotype Association", Genetics, vol. 202, 1345-1363, Apr. 2016.

* cited by examiner

*Primary Examiner* — Russell S Negin
(74) *Attorney, Agent, or Firm* — Jeffrey Schox; Diana Lin

(57) ABSTRACT

In variants, a method for genomic association can include: determining observed variable values and observed phenotype values for each organism in a population, removing information from variables of interest, determining a phenotype-variable association model, identifying causal variables associated with a phenotype, and/or any other suitable steps.

10 Claims, 30 Drawing Sheets

| | $V_1$ | $V_2$ | $V_3$ | $V_4$ | | $V_n$ | |
|---|---|---|---|---|---|---|---|
| organism A | 0 | 1 | 2 | 2 | | 0 | |
| organism B | 1 | 2 | 2 | 1 | | 1 | |
| organism C | 0 | 1 | 1 | 2 | | 0 | |
| organism D | 2 | 2 | 2 | 0 | | 1 | S100 |
| organism E | 2 | 1 | 0 | 0 | ... | 0 | observed data set |
| organism F | 2 | 1 | 1 | 1 | | 1 | |
| organism G | 2 | 2 | 2 | 0 | | 2 | |
| organism H | 0 | 0 | 0 | 0 | | 2 | |
| organism I | 1 | 0 | 1 | 1 | | 2 | |

FIGURE 11A

| | $V_1$ | $V_2$ | $T_2$ | $V_3$ | | $V_n$ | |
|---|---|---|---|---|---|---|---|
| organism A | 0 | 1 | 2 | 2 | | 0 | |
| organism B | 1 | 2 | 2 | 1 | | 1 | |
| organism C | 0 | 1 | 2 | 2 | | 0 | |
| organism D | 2 | 2 | 2 | 0 | | 1 | S450 |
| organism E | 2 | 1 | 1 | 0 | ... | 0 | test data set |
| organism F | 2 | 1 | 1 | 1 | | 1 | |
| organism G | 2 | 2 | 2 | 0 | | 2 | |
| organism H | 0 | 0 | 0 | 0 | | 2 | |
| organism I | 1 | 0 | 0 | 1 | | 2 | |

FIGURE 11B

| | $T_1$ | $T_2$ | $T_2$ | $T_3$ | | $T_n$ | |
|---|---|---|---|---|---|---|---|
| organism A | 1 | 2 | 2 | 2 | | 1 | |
| organism B | 1 | 2 | 2 | 1 | | 1 | |
| organism C | 0 | 0 | 2 | 2 | | 0 | |
| organism D | 2 | 1 | 2 | 1 | | 2 | S450 |
| organism E | 1 | 1 | 1 | 1 | ... | 1 | test data set |
| organism F | 1 | 1 | 1 | 0 | | 1 | |
| organism G | 2 | 2 | 2 | 0 | | 2 | |
| organism H | 0 | 0 | 0 | 0 | | 0 | |
| organism I | 1 | 1 | 0 | 0 | | 2 | |

FIGURE 11C

SYSTEM AND METHOD FOR GENOMIC ASSOCIATION

CROSS-REFERENCE TO RELATED APPLICATIONS

This application claims the benefit of U.S. Provisional Application No. 63/317,656 filed 8 Mar. 2022, U.S. Provisional Application No. 63/325,831 filed 31 Mar. 2022, U.S. Provisional Application No. 63/350,326 filed 8 Jun. 2022, and U.S. Provisional Application No. 63/350,328 filed 8 Jun. 2022, each of which is incorporated in its entirety by this reference.

TECHNICAL FIELD

This invention relates generally to the genomic field, and more specifically to a new and useful system and method in the genomic field.

BRIEF DESCRIPTION OF THE FIGURES

FIGS. 11A, 11B, and 11C depict illustrative examples of an observed data set, a test data set with information for one variable replaced, and a test data set with information for all variables replaced, respectively.

DETAILED DESCRIPTION

The following description of the embodiments of the invention is not intended to limit the invention to these embodiments, but rather to enable any person skilled in the art to make and use this invention.

1. Overview

Figure 1:
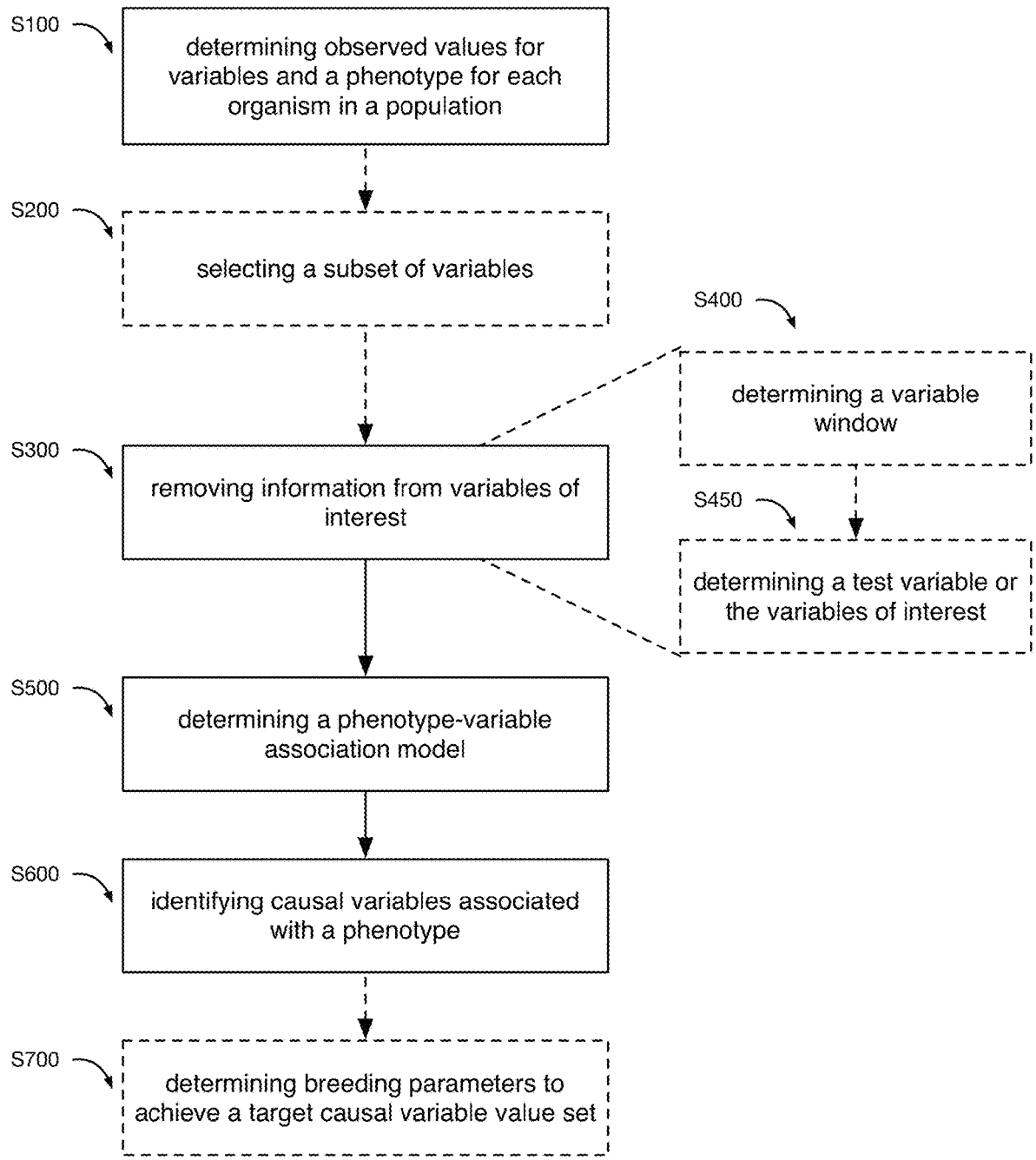
FIG. 1 is a schematic representation of a variant of the method.

As shown in FIG. 1, the method can include: determining observed values for variables and phenotypes for each organism in a population S100, removing information from variables of interest S300, determining a phenotype-variable association model S500, identifying causal variables associated with a phenotype S600, and/or any other suitable steps. In variants, the method can function to identify genomic components, environmental parameters, and/or other variables linked to (e.g., causing or influencing) a target phenotype.

2. Examples

In an example, the method for determining a variable's association with a phenotype can include: observing a genotype and phenotype for each organism in a population; aggregating the phenotype values from each organism into an observed phenotype (P) (e.g., a vector of the phenotype values); and determining an observed variable ($V_i$) for each of a set of variables (e.g., a vector of the genotype values and/or optionally other variable values such as environmental parameters, methylation, etc.). In this example, each observed variable can be a vector of observed values (e.g., a vector of alleles, a vector of k-mers, a vector of RNA transcription amounts, etc.) for the respective variable, constructed across the population of organisms (e.g., wherein the observed variable and observed phenotype have the same organism ordering). In variants, the method can optionally include selecting a subset of variables, wherein the remainder of the method can be limited to analysis of the variables corresponding to the variable subset; alternatively, the method can be performed for all variables.

The influence of each variable on the phenotype can then be determined by: generating a test variable (e.g., substitute variable) for a variable of interest to replace the corresponding observed variable; generating one or more phenotype-variable association models based on the test variable, the observed variables, and the observed phenotype; determining an observed model metric and a test model metric for the model; and determining the influence of the variable on the phenotype based on a comparison between the observed and test model metrics. In examples, the model metric can be: the variable weight (e.g., coefficients), the model's loss, the model's variance (e.g., coefficient of determination), and/or be any other model metric.

The test variable can optionally have the same statistical distribution as the respective observed variable, but not be generated using information from said observed values. In an example, the test variable can be determined by: determining (e.g., fitting, training, etc.) a variable-variable association model using observed variables, wherein the resultant model (e.g., wherein the variable of interest is treated as the dependent variable and the other observed variables are treated as independent variables) can then be used to calculate the test variable. For example, the variable-variable association model can be used to calculate test values for each organism based on the observed values for other variables for the organism.

In a specific example, the influence of each variable can be determined by: determining test variables for each variable; and calculating a single regression between the observed phenotype (e.g., the dependent variable) and a combined matrix (e.g., the independent variables) that includes both the test variables and their respective observed counterpart variables (e.g., the original genotypes). Highly-influential variables can be identified based on the difference between the coefficient of the respective test variable and the coefficient of the respective observed variable (e.g., where the variables with the highest coefficient difference can be treated as the most influential).

However, the method can be otherwise performed.

3. Technical Advantages

Variants of the technology can confer one or more advantages over conventional technologies.

First, it is oftentimes difficult to determine which specific variables (e.g., genomic components such as genes, loci, genomic regions, etc.; environmental parameters; gene expression; etc.) cause and/or are associated with a given phenotype. Conventional methods of individually editing and testing genes is an intractable approach due to the inherent size of the genome. This problem is compounded because phenotypes can be polygenic, so both individual gene-phenotype effects and gene combination-phenotype effects need to be tested—the number of testing permutations required is immense, and would require decades of data gathering. The inventors have discovered that causal variables can be identified in a highly efficient manner by modeling the relationship between a trait (e.g., phenotype) and a set of variables (e.g., genomic components), removing the information unique to a genomic component of interest from the model, and comparing the model's performance with and without the genomic component's information—the more the model's performance degrades when the genomic component information is removed, the more causal the genomic component.

Second, it is incredibly difficult to ensure the stand-in information (e.g., test variable) used to stand-in for the original information (e.g., observed variable) has the same statistical distribution as the original variable's information without using the original variable information. To solve this, the inventors have further discovered that values for other variables (e.g., neighboring variables selected using a variable window) can be used to generate acceptable stand-in information, leveraging the fact that neighboring genes are oftentimes correlated and/or share an evolutionary history), thereby mitigating or eliminating original information leakage into the test variable, and increasing predictive power.

Third, the large dimensionality of the search space presents a significant computational load problem. In a first example, the inventors have discovered that by computing a regression with both original and stand-in information (e.g., where the coefficients for the observed variables and test variables can then be compared for each variable), an association metric for each variable can be computed faster and with a lower computational load. In a second example, variants of the technology can reduce the dimensionality by pre-selecting a variable subset (e.g., using clustering techniques, with an initial regression to determine a subset of genomic components that are associated with variables that have nonzero coefficients, etc.). In a third example, the inventors have discovered that by adaptively selecting a variable window (e.g., identifying a smaller number of variables correlated with variables of interest), a lower dimensional model (e.g., low-dimension linear regression) can be used to determine the test variable. In a fourth example, the inventors have discovered that models (e.g., generative models, autoencoders, etc.) can output multiple test variables, which can significantly increase computational speed. In a fifth example, an encoder can be trained on other variables (e.g., trained on genomic component values elsewhere in a genome, far from the variables of interest), then iteratively implemented (e.g., without re-training) to generate each new test variable. In a sixth example, the inventors have discovered that test variables can be generated in a reduced dimension space (e.g., a latent space), wherein the causal variables can be identified in the reduced dimension space.

Fourth, in variants, simplifying assumptions can be made such that identifying variables associated with a phenotype is a tractable problem. In a first example, there are a significant number of genomic components (e.g., loci) for a single model, so a univariate model for each genomic component can be implemented. In a second example, population structure is unknown and difficult to quantify, so principal component analysis and/or kinship analysis can be used to correct for structure. In a third example, the effect of certain genomic components can depend on the environment, so a separate analysis can be performed in separate environments. In a fourth example, many genomic components interact to generate a phenotype, so the assumption can be made that epistasis is small enough to be ignored. However, other assumptions can be implemented.

Fifth, variants of the technology can reduce the dimensionality of the search space by identifying causal variables (e.g., conditional model reliance features). For example, a phenotype model (e.g., updated phenotype-variable association model) can be generated using only the causal variables. Since the causal variables represent only a subset of all potential variables, the (updated) phenotype-variable association model can: include inter-variable interactions, be a low-dimensional regression, be used to determine target causal variable values using more computationally efficient and accurate optimization techniques (e.g., convex optimization with a single solution), and/or provide other advantages.

Sixth, variants of the technology can identify a set of target causal variable values (e.g., a target set of alleles, a target set of environmental parameters, etc.) before attempting to predictively breed organisms. This can be more computationally efficient (e.g., by limiting the number of variables that are used in a predictive breeding algorithm)

and result in better-optimized organisms and growing environments (e.g., by avoiding local minima during optimization). For example, a hypothetical target organism with a target set of randomly-generated causal variable values resulting in the best phenotype (e.g., the most performant trait) for a given growing environment can be identified before attempting to generate the optimal variable values biologically through breeding. In another example, the hypothetical target organism, the environmental variable values, and/or treatment values (e.g., DNA methylation treatments) resulting in the most performant trait can be identified before attempting to predictively breed the existing organisms.

However, further advantages can be provided by the system and method disclosed herein.

4. Method

As shown in FIG. 1, the method can include: determining observed values for variables and phenotypes for each organism in a population S100, removing information from variables of interest S300, determining a phenotype-variable association model S500, identifying causal variables associated with a phenotype S600, and/or any other suitable steps. The method can optionally include selecting a subset of variables S200, determining breeding parameters to achieve a target causal variable value set S700, and/or any other suitable steps.

All or portions of the method can be performed once (e.g., for a phenotype, for a species, for a variable, etc.), multiple times, iteratively (e.g., for each phenotype in a set, for each variable in a set, etc.), in real time (e.g., responsive to a request), concurrently, asynchronously, periodically, and/or at any other suitable time. All or portions of the method can be performed automatically, manually, semi-automatically, and/or otherwise performed.

All or portions of the method can be performed using a computing system, using a database (e.g., a system database, a third-party database, etc.), using a genomic sequencer, using assay tools, using measurement systems, by a user, and/or by any other suitable system. The computing system can include one or more: CPUs, GPUs, custom FPGA/ASICS, microprocessors, servers, cloud computing, and/or any other suitable components. The computing system can be local, remote, distributed, or otherwise arranged relative to any other system or module.

The method can be used with one or more models, including variable-variable association models, phenotype-variable association models, analysis models, variable window models, process models, and/or any other model. The models can include or use: regression (e.g., linear, nonlinear, multivariate, leverage regression, etc.), classification, neural networks (e.g., CNN, DNN, CAN, LSTM, RNN, etc.), rules, heuristics, equations (e.g., weighted equations, etc.), selection (e.g., from a library), instance-based methods (e.g., nearest neighbor), regularization methods (e.g., ridge regression), decision trees (e.g., random forest), Bayesian methods (e.g., Naïve Bayes, Markov, hidden Markov models, etc.), kernel methods, deterministics, genetic programs, encoders (e.g., autoencoders), support vectors, ensemble methods, association rules, optimization methods (e.g., Bayesian optimization, convex optimization, non-convex optimization, multi-objective optimization, etc.), statistical methods (e.g., probability), comparison methods (e.g., matching, distance metrics, thresholds, etc.), dimensionality reduction (e.g., principal component analysis, t-distributed stochastic neighbor embedding, linear discriminant analysis, partial least squares regression, Sammon mapping, multidimensional scaling, projection pursuit, etc.), clustering methods (e.g., k-means clustering, hierarchical clustering, expectation maximization, etc.), generative models, process models, biological models, and/or any other suitable method. Models can use classical or traditional models, machine learning models, and/or be otherwise configured. Models can be low-dimension models, high-dimension models, and/or otherwise configured.

Models can be trained, learned, fit, predetermined, and/or can be otherwise determined. Models can be trained using self-supervised learning, semi-supervised learning, supervised learning, unsupervised learning, transfer learning, reinforcement learning, and/or any other suitable training method.

The method can be used with variables. Variables are preferably characteristics associated with an organism, but can be otherwise defined. Examples of variables include: genomic components (e.g., genomic variables), gene expression (e.g., which gene and/or variant thereof are expressed, transcribed, etc.; DNA and/or RNA expression) (e.g., gene variables), protein expression (e.g., which proteins are expressed) (e.g., protein variables), methylation (e.g., which DNA positions are methylated, overall amount of methylation, etc.), environmental variables (e.g., environmental parameters, such as temperature, light, heat, soil quality, nutrient composition, water availability, land grade, treatment application frequency, etc.), transcriptome variables (e.g., RNA locus, RNA transcript identifier, RNA region, a gene corresponding to an RNA transcript, etc.), protein binding variables, microbial variables (e.g., for microbes associated with the organism), and/or any other characteristic associated with an organism. Genomic components are preferably basic units shared across all organisms of a population (e.g., a species), but can alternatively be otherwise defined. Examples of genomic components include: a gene, a gene group, a locus (e.g., DNA or RNA), a gene region, RNA region, RNA transcript identifier, k-mer, and/or any other genomic component. Examples of environmental variables include: temperature; pressure; light; humidity; concentration and/or distribution of macronutrients and/or micronutrients (e.g., nitrogen, phosphorous, etc.); growing duration, treatment frequency, and/or any other temporal characteristic thereof; and/or any other characteristic of an organism's environment. The set of variables (e.g., a plurality of variables) preferably includes all variables, but can alternatively include a subset of the variables (e.g., the variables that can be controlled, etc.), and/or be otherwise defined. For example, the variable set can include: all possible loci, loci of interest, all possible genes (e.g., all genes of one or more organisms in the population), expressible protein, environmental variables, genes of interest, all genomic regions (e.g., nonoverlapping or overlapping), genomic regions of interest, all methylated locations, methylated locations of interest, DNA and/or RNA sequences, all environmental parameters, environmental parameters of interest, and/or any other variables.

Variable values are preferably a measure of the organism's value for the given variable, but can be otherwise defined. Variable values can be qualitative, quantitative, relative, discrete, continuous, a classification, numeric, binary, and/or be otherwise characterized. In a first example, genomic component values can include: genotypes, DNA and/or RNA sequences, single nucleotide polymorphisms (SNPs), k-mers, k-mer counts, RNA counts, allele locations, presence/absence of a genomic component (e.g., of a particular gene sequence), evolutionary history, heredity history, DNA fragmentation, and/or any other genetic and/or cellular information. In a specific example, a genomic component value can be a numerical value representing the genotype (e.g., an allele coding) for an organism at a gene locus associated with the variable. In examples, an allele coding can include a 0, 1, or 2 value (e.g., determined based on allele frequency in the population) and/or any other values (e.g., 0-9 values when more than two copies of an allele are present in the population). In a second specific example, a genomic component value can be a numerical value representing the k-mer count for an organism for a k-mer associated with the variable. Genomic component values can optionally include and/or correspond to a set of genetic information (e.g., a set of genes, a set of SNPs, a set of k-mers, a raw DNA sequence, etc.). In a second example, gene expression values can include: RNA concentration; whether or not a given gene has been expressed, and/or other measures of gene expression. In a third example, protein expression values can include: whether a given protein is expressed, concentration of each protein, and/or other measures of protein expression. In a fourth example, methylation values can include: a ratio between the number of times a gene is methylated and the number of times a gene is sequenced (e.g., methylation fraction), and/or other measures of methylation. In a fifth example, environment values can include: temperature values, pressure values, nutrient concentration in the growing medium, moisture level in the growing medium, humidity level, ultraviolet light level, and/or other measures of environmental or growing variables. In a sixth example, transcriptome variable values include: RNA sequences, RNA expression (e.g., RNA transcription for a given gene or allele), quantity of RNA transcript, transcription amount of a given RNA sequence or gene, and/or other transcriptome values. In a seventh example, protein binding variables can include a measure of protein binding affinity, and/or any other protein binding values. In an eighth example, species abundance counts for a microbial community on/near the organism, and/or any other microbial information values. However, variables and/or variable values can be otherwise defined.

The method can be used with phenotypes (e.g., traits). The phenotype is preferably an observable characteristic or trait of the organisms, but can be otherwise defined. Phenotype values can be qualitative, quantitative, relative, discrete, continuous, a classification, numeric, binary, and/or be otherwise characterized. Examples of phenotype values can include: drought resistance metric, salt resistance metric, heat resistance metric, contaminant resistance metric, a macronutrient parameter and/or micronutrient parameter (e.g., density, composition, etc.), mass, height, appearance (e.g., color), compound processing (e.g., amount of nitrogen fixation, amount of heavy metal fixation, etc.), and/or any other trait values. In variants, the phenotype can be treated as a variable. However, phenotypes and/or phenotype values can be otherwise defined.

Each variable and/or phenotype can be a vector including the values (e.g., observed values and/or test values) for the respective variable or phenotype for each of a set of organisms (e.g., ordered set of organisms). The values can be observed values (e.g., from experiments or measurements); predicted, simulated, or otherwise generated values (e.g., predicted from genetic mutation simulations, predicted using cross-breeding simulations, test values determined via S450 etc.); and/or otherwise determined. In a first example, a genomic component variable can be a vector of genomic component values (e.g., representing genotypes corresponding to the genomic component, representing k-mers corresponding to the genomic component, etc.) with one genomic component value in the vector for each organism in the population. In a second example, a phenotype variable can be a vector of phenotype values (e.g., representing the presence and/or absence of one or more traits, representing a collection of traits, etc.) with one phenotype value for each organism in the population. However, the phenotype and/or variables can be otherwise represented.

Determining observed values for variables and phenotypes for each organism in a population S100 functions to determine information (e.g., observed values) used for predicting association between variables and/or between phenotypes and variables. S100 can be performed before S200, before S300, and/or at any other time. S100 can optionally be performed one or more times: for each organism in a population of organisms, for each phenotype in a phenotype set, for each variable in a phenotype set, and/or at any other time.

The organisms in the population (e.g., set of organisms) are preferably of the same species, but can alternatively be of different species. The organisms can be any plant, animal, fungi, protist, moneran, and/or any other organism. In illustrative examples, the organisms can be algae, broccoli, radishes, strawberry, dandelions, corn, bamboo, potatoes, mushrooms, herbs, pigs, cows, chickens, and/or any other organisms. In specific examples, the organisms can be used as food products, used to manufacture food products (e.g., as an ingredient in a food product), used to manufacture materials (e.g., rubber, oil, etc.), and/or used for any other purposes.

S100 can include: for each organism, determining observed values for each variable in a set of variables; for each organism, determining observed values for each phenotype in a set of phenotypes; determining an observed variable for each of the set of variables based on the observed variable values; and determining an observed phenotype for each of the set of phenotypes based on the observed phenotype values. The set of variables preferably includes multiple variables, but can alternatively include a single variable. The set of phenotypes is preferably a single phenotype (e.g., representing a single trait, representing an aggregate of traits, etc.), but can alternatively include multiple phenotypes.

The observed values for variables for each organism and/or the observed values for phenotypes for each organism can be determined by: retrieving values from a database, genotyping, observing (e.g., measuring, sequencing, analyzing measurements, etc.), analyzing sequences, simulating/predicting (e.g., using a model, using cross-breeding and/or mutation simulations, etc.), aggregating values (e.g., aggregating multiple observed values for an organism to determine an aggregate observed value), transforming values (e.g., converting qualitative values to quantitative values), a combination thereof (e.g., using different methods for different variables and/or phenotypes), and/or any other method of determining organism information. Sequencing can include DNA sequencing, RNA sequencing, k-mer counting, and/or any other genetic component measurement. Determining observed values for phenotypes and/or variables can optionally be performed after the physical organism is grown and/or harvested, during growth and/or harvesting, and/or at any other stage. In specific examples, determining observed values for a physical organism can include: phenotyping the organism and optionally converting the organism's phenotype into a numerical value (e.g., using a scoring method, ranking method, rating method, mapping, comparison methods, etc.) to determine the respective observed phenotype value; sequencing genomic components to determine the respective observed variable value(s); measuring/recording environmental conditions (e.g., growth conditions) for the organism to determine the respective observed variable value; retrieving predetermined environmental conditions to determine the respective observed variable value; measuring gene expression to determine the respective observed variable value; measuring DNA methylation to determine the respective observed variable value; using a known relationship (e.g., regression, neural network, any other model, lookup table, etc.) between a first variable (e.g., environmental variable) and a second variable (e.g., expression of a gene) to predict the observed values for the first variable, and/or any other method of determining values for variables and/or phenotypes.

Determining an observed variable for each variable in the set of variables can include aggregating observed variable values across the organisms to form a vector (e.g., a numerical vector). The observed variable is preferably a vector of observed variable values for a corresponding variable (e.g., where all variable values in the observed variable vector are associated with the same variable), but can be otherwise constructed. However, the method can include any other observed variable to variable cardinality (e.g., where each variable is associated with more than one observed variable vector and/or vice versa). In a specific example, each element of the observed variable vector includes an observed value for a different organism (e.g., each observed variable includes an observed value for the corresponding variable from each organism in the population). In an illustrative example, the observed variable for a particular genomic component includes an allele coding value from each organism for that genomic component. In variants, observed variables can function as independent variables in all or parts of the method.

Observed values within each observed variable are preferably ordered by organism (e.g., such that vector elements correspond to the same organism order across observed variables), but can alternatively be otherwise arranged. Multiple observed variables (e.g., observed variables for the genomic components of the species' genome) can optionally be aggregated into an observed data set (e.g., a matrix, a vector of variables, a set, a design matrix, etc.). An example is shown in FIG. 11A. In a first example, the observed variables are organized within the data set (e.g., matrix column order, vector order, set order, etc.) based on a locus associated with the respective genomic component of each variable. In a second example, the observed variables are unordered within the data set. In a third example, the observed variables are organized within the data set based on association metrics for each variable. However, the observed variables can be otherwise organized.

Determining an observed phenotype can include aggregating observed phenotype values across the organisms to form a vector (e.g., a numerical vector). The observed phenotype is preferably a vector of observed variable values for a corresponding phenotype (e.g., where all phenotype values in the observed phenotype vector are associated with the same phenotype), but can be otherwise constructed. However, the method can include any other observed phenotype to phenotype cardinality (e.g., where each phenotype is associated with more than one observed phenotype vector and/or vice versa). In a specific example, each element of the observed phenotype vector includes an observed value for a different organism (e.g., each observed phenotype includes an observed value for the corresponding phenotype from each organism in the population). In an illustrative example, the observed phenotype for a particular genomic component includes a trait value from each organism for that phenotype. In variants, observed phenotypes can function as dependent variables in all or parts of the method. Observed values within a phenotype are preferably ordered by organism (e.g., such that vector elements correspond to the same organism order across phenotypes and variables), but can alternatively be otherwise arranged.

However, observed values for variables and/or phenotypes can be otherwise determined.

The method can optionally include selecting a subset of variables S200, which functions to reduce the number of variables to analyze. In variants, selecting a subset of variables (e.g., subsampling the variables) can decrease computational load, increase analysis speed, transform high-dimensional data to low-dimensional data, enable low-dimension models (e.g., low-dimension regressions, low-dimension statistics, etc.), enable the use of convex optimization methods (e.g., strictly convex optimization methods, with a single solution), and/or provide other advantages. S200 can be performed after S100, before S300 (e.g., to determine which variables to use when removing information), before S400 (e.g., to determine which variables from which to select the variable window), and/or at any other time. The set of variables can optionally be adjusted to include only the variables corresponding to the subset of variables. In all or parts of the method, the set of variables can refer to the subset of variables.

In a first variant, the variable subset is selected from the variable set by manually specifying the variables (e.g., loci).

In a second variant, the variable subset is automatically selected. In examples, the variable subset can be selected based on: the evolutionary history of the population, linkage disequilibrium analysis, previous iterations of the method, information from S100, principal component analysis, kinship analysis, variable analysis parameters, coinheritance (e.g., a genome segment that is coinherited), and/or otherwise selected.

Figure 3:
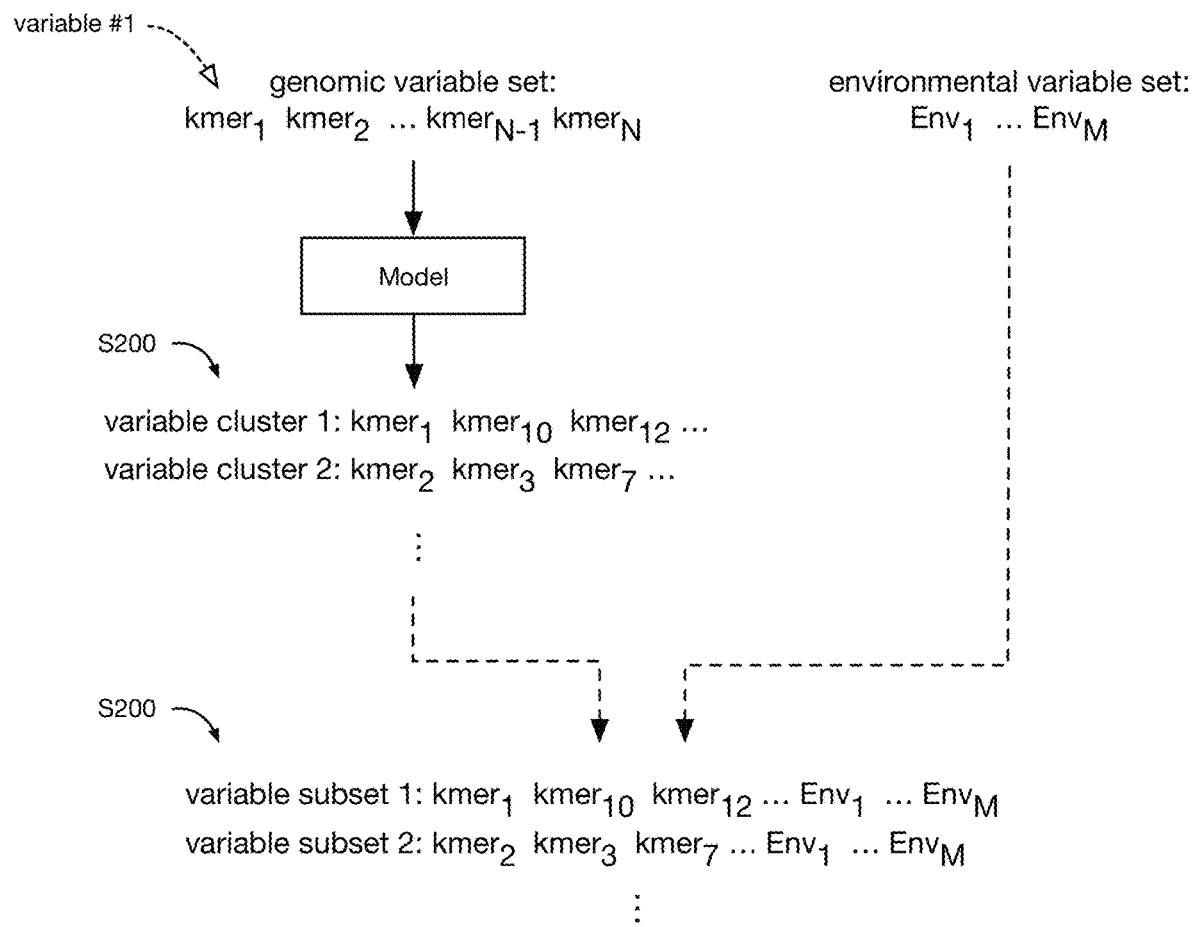
FIG. 3 depicts an example of selecting a subset of variables, including clustering k-mer variables.

In a third variant, the variable subset is selected using a model. In a first embodiment, the model is a phenotype-variable association model (e.g., a regression) including observed variables for each of the set of variables, wherein the variable subset is selected based on association metrics (e.g., regression coefficients, any association metric in S600, etc.) for each variable. In a first specific example, the variables corresponding to observed variables that have nonzero coefficients are selected. In a second specific example, the variables corresponding to observed variables that have a coefficient and/or absolute value of a coefficient above a threshold are selected. In a second embodiment, the model is used to cluster observed variables, wherein each cluster is a variable subset (e.g., the variables associated with observed variables in a cluster form a variable subset); an example is shown in FIG. 3. In examples, observed variables (e.g., k-mers) can be clustered based on variable analysis parameters. For example, linked or otherwise correlated observed variables can optionally be clustered together. In a specific example, k-mer variables can be clustering using k-means clustering, wherein the k is specified such that no cluster exceeds a threshold variable subset size. However, any other clustering method can be used.

Figure 2:
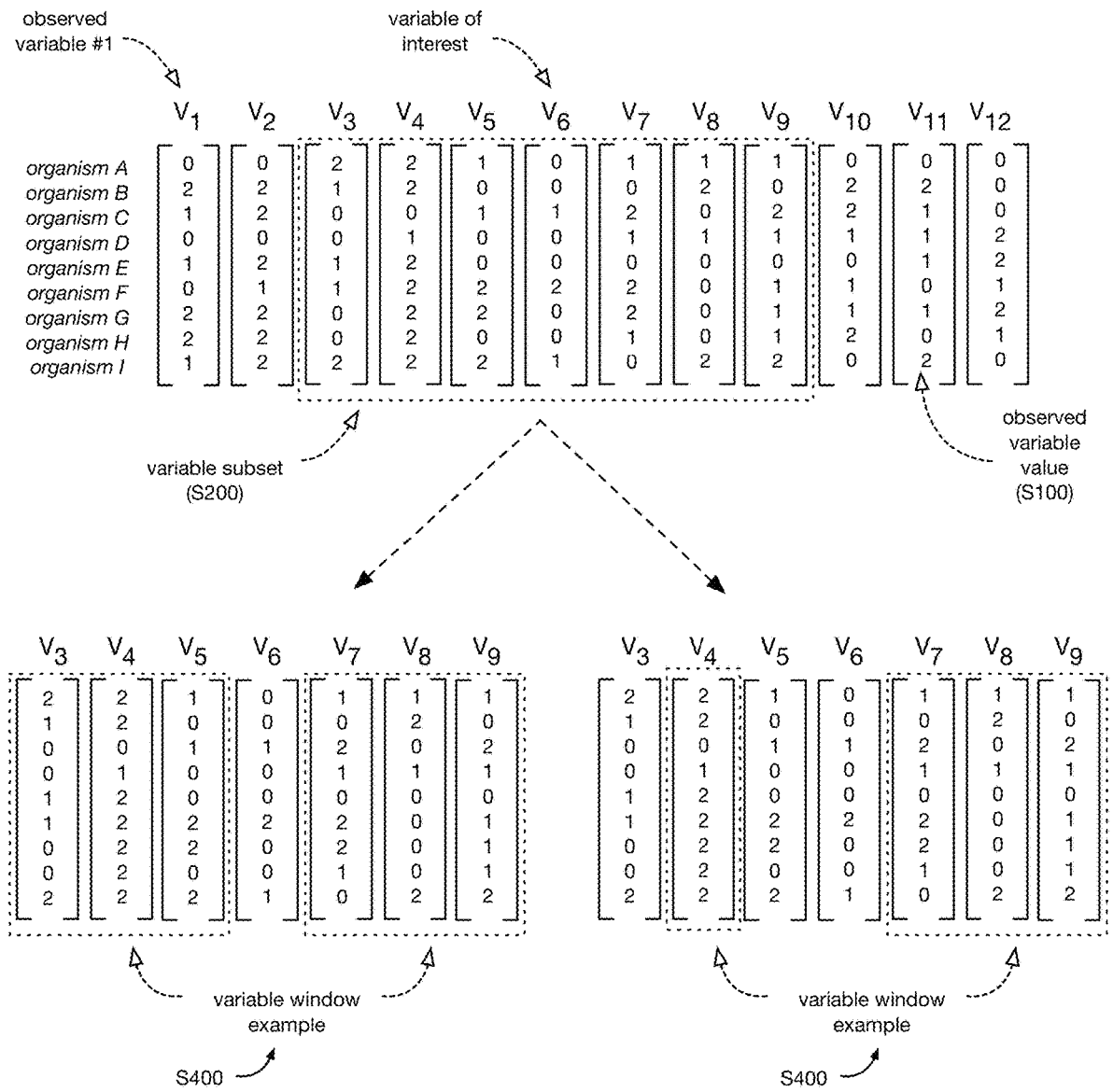
FIG. 2 depicts an example of selecting a subset of variables and determining a variable window within the subset of variables.

In a fourth variant, the variable subset is determined using variable window selection methods (e.g., described in S400). For example, the variable subset can be selected based on the variable(s) of interest (e.g., wherein the subset includes variables flanking the variable(s) of interest, etc.). An example is shown in FIG. 2.

However, the variable subset can be selected: randomly, by shuffling the variable subset (e.g., iteratively removing less-active or less-influential variables and selecting new variables), resampled until a test variable quality is met (e.g., the fit quality, the $R^2$ of the model fit, the RMSE, the log likelihood difference, the similarity between the test variable distribution and the variable of interest's distribution, etc.), quality is met and/or otherwise selected.

However, any variable selection method can be used.

The variable analysis parameters can include: autocorrelation analysis (e.g., patterns), linkage disequilibrium analysis, evolutionary history of the population, principal component analysis, kinship analysis, variable location, correlation strength, effective population size, summary statistics (e.g., distribution, parameters of a variable-variable association model or phenotype-variable association model using the variables, etc.), and/or any other variable analyses. In a specific example, an analysis model can be used to determine (e.g., extract) the analysis parameters based on observed variables (e.g., an observed variable dataset). In a second specific example, the variable analysis parameters can be retrieved from a dataset.

The variable subset can be symmetric relative to variable(s) of interest or non-symmetric. The variable subset can optionally be selected such that the number of variables is less than a threshold number. In an example, when the number of organisms in the population is N, the threshold number can be between 0.1*N-10*N or any range or value therebetween (e.g., 0.5*N-1*N, N, N*⅔, etc.), but can alternatively be less than 0.1*N or greater than 10*N. In another example, the threshold number can be between 10 loci-5000 loci (e.g., 50 loci-250 loci), but can alternatively be less than 10 loci or greater than 5000 loci. In another example, the threshold number can be between 500 bases-10,000 kilobases (e.g., 1 kilobases-10 kilobase), but can alternatively be less than 500 bases or greater than 10,000 kilobases.

Selecting the variable subset can optionally include selecting a subset of a variables corresponding to a first variable type (e.g., genomic component variables), and selecting all environmental variables of a second variable type (e.g., environmental variables). An example shown in FIG. 3.

However, the variable subset can be otherwise determined.

Removing information from variables of interest S300 can function to remove the variable's influence on the phenotype (in a phenotype-variable association model). S300 can be performed after S100, after S200, iteratively for each variable in a set (e.g., across the observed data set), and/or at any other time.

S300 can be performed for one or more variables of interest in the set of variables (e.g., concurrently and/or serially). S300 is preferably performed for a single variable of interest (e.g., each iteration of S300 is performed for a single variable of interest), but can alternatively be performed for multiple variables of interest (e.g., determining a single test variable corresponding to a set of variables of interest). The variables of interest can be: manually selected, automatically selected (e.g., wherein each iteration of S300 includes a subsequent variable of interest), randomly selected and/or otherwise selected from the set of variables. The set of variables can be: the variable subset determined in S200 (e.g., where the observed data set includes only those variables in the subset of variables), all variables used in S100 (e.g., all genomic components in the genome), and/or any other set of variables.

Removing information from a variable of interest can include replacing and/or otherwise changing the observed variable associated with the variable of interest. In a first variant, removing information includes removing the observed variable from a phenotype-variable association model (e.g., where the model predicts phenotype values without using the observed variable). In a second variant, a test variable (with test values) can be determined as a replacement for the observed variable. For example, S300 can include determining a variable window (e.g., S400) and determining test values for the variable(s) of interest using the variable window (e.g., S450). However, information can be otherwise removed.

The method can optionally include determining a variable window S400, which can function to determine a subset of variables, wherein the corresponding observed variables can be used to predict a test variable for the variable(s) of interest (e.g., wherein the variable corresponding to the test variable is not within the variable window). In a specific example, the variable(s) of interest and the variable window can both be within the variable subset determined in S200 (e.g., within a shared k-mer cluster).

The variable window size and/or other parameters can be fixed or variable (e.g., based on the variable of interest). The variable window size is preferably less than a threshold number of variables. In an example, when the number of organisms in the population is N, the threshold number can be between 0.1*N-10*N or any range or value therebetween (e.g., 0.5*N-1*N, N, N*⅔, etc.), but can alternatively be less than 0.1*N or greater than 10*N. In another example, the threshold number can be between 10 loci-5000 loci (e.g., 50 loci-250 loci), but can alternatively be less than 10 loci or greater than 5000 loci. In another example, the threshold number can be between 500 bases-10,000 kilobases (e.g., 1 kilobases-10 kilobase), but can alternatively be less than 500 bases or greater than 10,000 kilobases. The variable window is preferably positioned relative to the variable of interest (e.g., centered about the variable of interest, offset from the variable of interest, start or end from the variable of interest, be within a threshold distance from the variable of interest, etc.), but can be otherwise positioned. The variable window can be symmetric about the variable of interest (e.g., including optional truncation or wrapping when the variable is at an end of a variable set) or non-symmetric.

The variable window can be manually determined, determined using a model (e.g., a variable window model, a variable-variable association model, etc.), predetermined, randomly determined, and/or otherwise determined.

In a first variant, the variable window is fixed relative to the variable of interest. In a first example, the variable window can be a fixed size, and positioned symmetric about the variable of interest (e.g., wherein the variable window includes two flanks on either side of the variable of interest in the variable set). In a second example, the variable window includes all variables in the subset of variables (e.g., S200).

Figure 4:
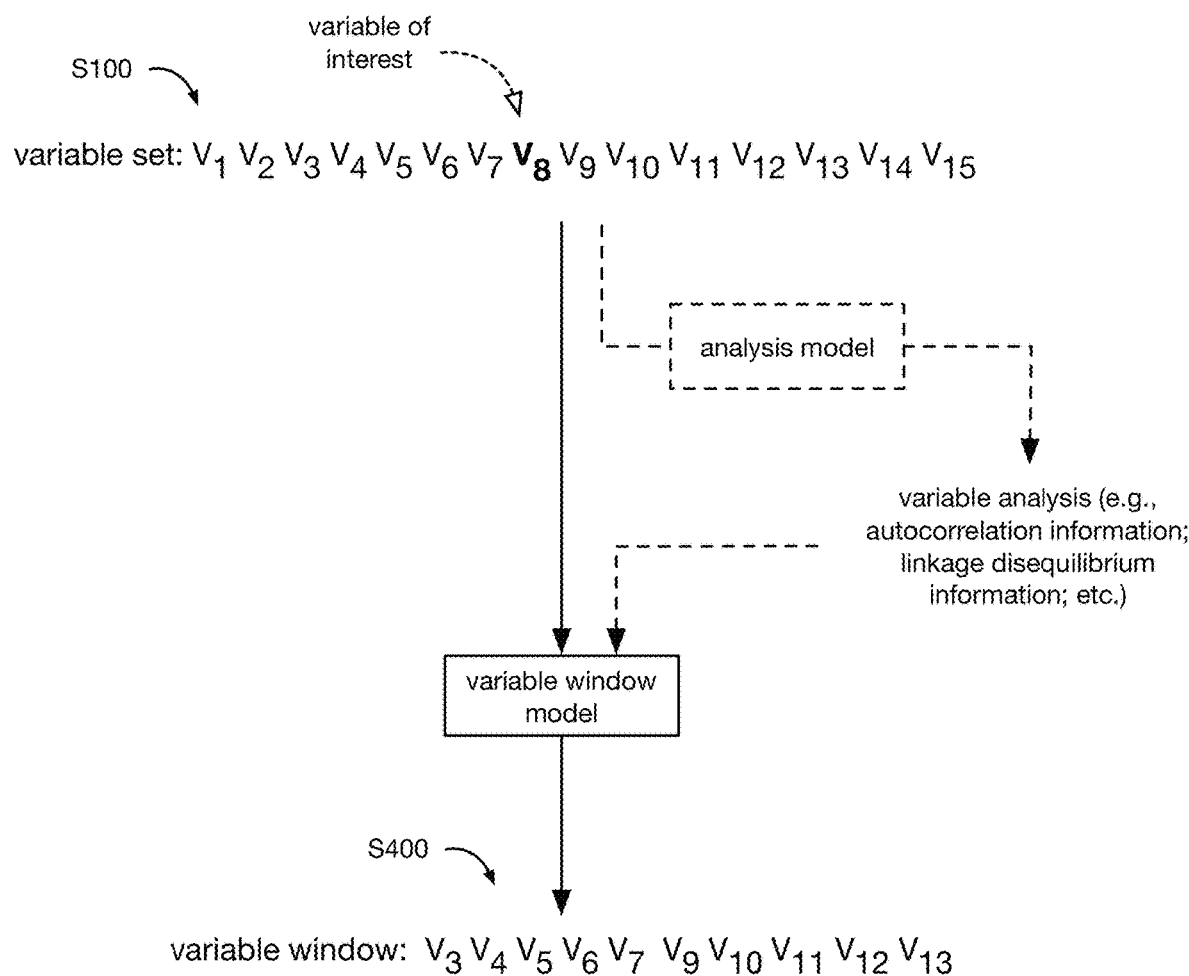
FIG. 4 depicts an example of determining a variable window based on variable analysis parameters.

In a second variant, the variable window can be determined based on variable analyses. For example, the variable window can vary dynamically based on the variable analysis parameters associated with the variable of interest. In examples, the variable window can be determined based on: linkage disequilibrium (e.g., wherein the variable window includes or excludes other variables in linkage disequilibrium with the variable of interest); variable of interest location (e.g., known location, predicted location, etc.); local autocorrelation patterns; correlation strength (e.g., wherein the variable window includes other variables tightly correlated with the variable of interest); and/or otherwise determined. An example is shown in FIG. 4.

In a third variant, the variable window can be adaptively determined. For example, the variable window can be iteratively re-determined (e.g., using a variable window model) until one or more criteria are satisfied. The criteria can include a variable window evaluation metric criterion (e.g., the variable window evaluation metric rising above a threshold), a number of iterations, a number of iterations without an increase in the model metric, completing a cycle through all variables in the variable set (e.g., in the variable subset), a threshold criterion, and/or any other criterion. The variable window evaluation metric is preferably a model metric for a variable-variable association model (e.g., any model metric described in S600), wherein the variable-variable association model is used to determine a test variable for the variable of interest based on observed variables for variables in the (current iteration) variable window. For example, the variable-variable association model can be re-determined (e.g., re-trained) in each iteration. Alternatively, the variable window evaluation metric can be any other assessment of test variable determination.

Figure 5A:
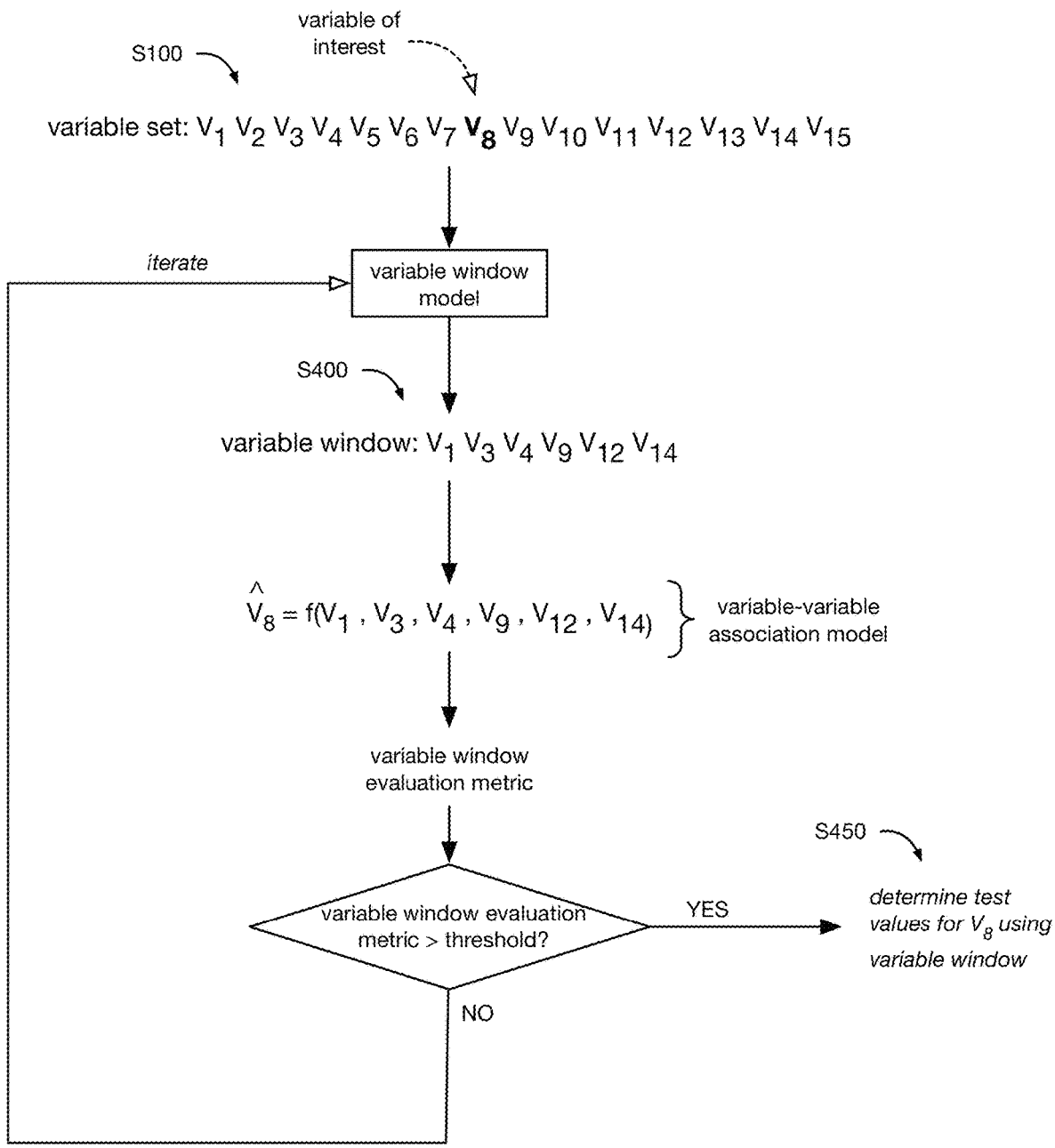
FIGS. 5A and 5B depict examples of iteratively determining a variable window.
Figure 5B:
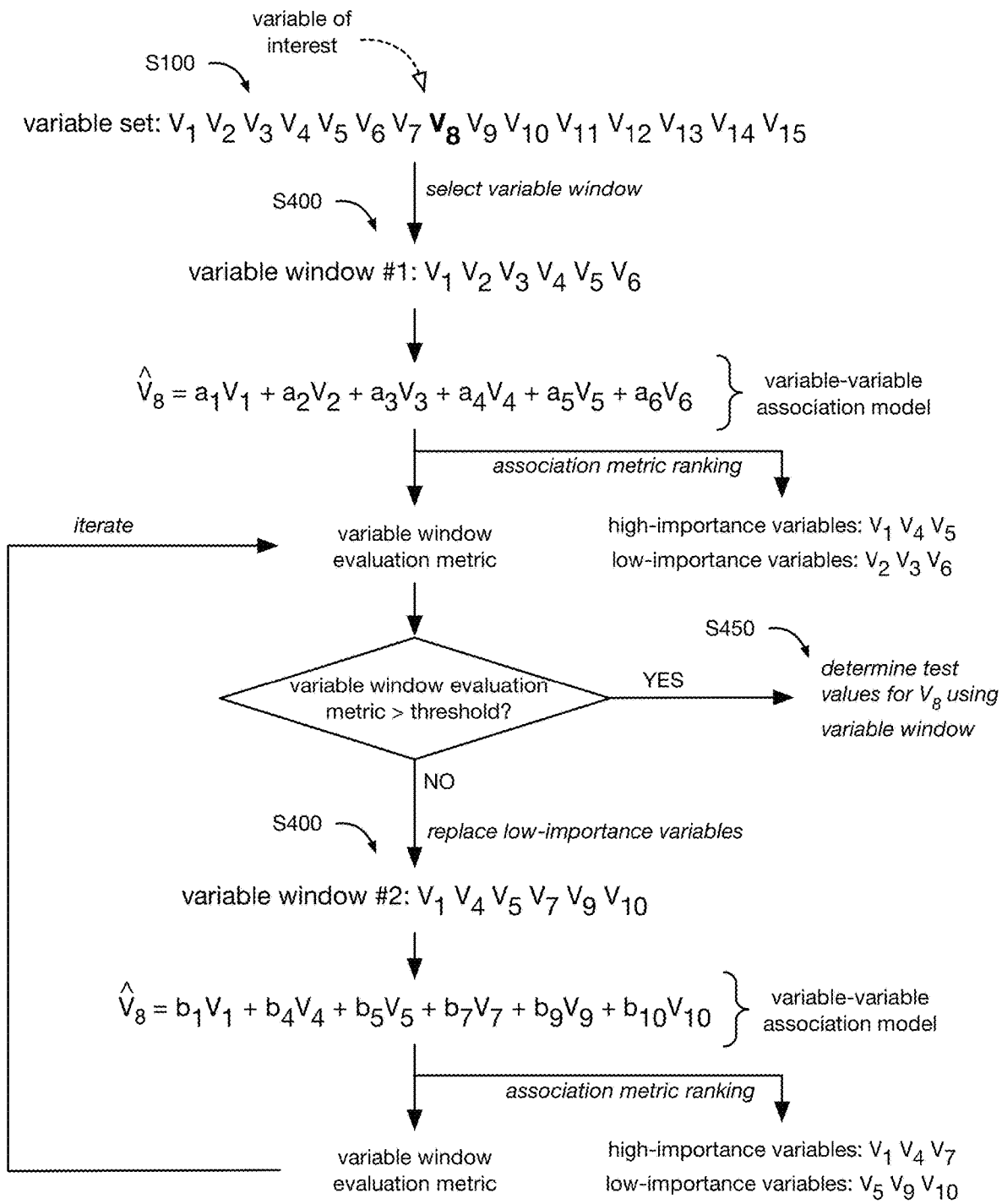

In a first example, in each iteration, the variables in the variable window are randomly selected from the variable set (e.g., the variable subset). An example is shown in FIG. 5A. In a second example, the variable window is segmented into high-importance variables (e.g., an active set) and low-importance variables (e.g., a shuffled set) based on an association metric for each variable in the variable window (e.g., association metrics as described in S600, for the variable-variable association model), wherein the association metrics are determined based on the variable-variable association model. In each iteration, the low-importance variables are then replaced with new variables, and the variable window is re-segmented for the next iteration (e.g., wherein a new variable can replace a high-importance variable if the association metric for the new variable is above the association metric for the high-importance variable). An example is shown in FIG. 5B.

However, the variable window can be otherwise determined.

The method can optionally include determining a test variable for the variable(s) of interest S450, which can function to generate a variable to stand-in for one or more corresponding observed variables (e.g., used as inputs in in a phenotype-variable association model), to generate a negative control for one or more observed variables, to remove information from one or more observed variables (e.g., while maintaining a suitable variable form and/or distribution such that an original observed variable can be exchanged with its corresponding test variable), and/or to otherwise perturb one or more observed variables. The test variable preferably has the same or substantially the same distribution (e.g., statistical distribution) as the observed variable associated with the same variable of interest, but alternatively can have a different distribution. S450 can be performed after S400 and/or at any other time.

Figure 9:
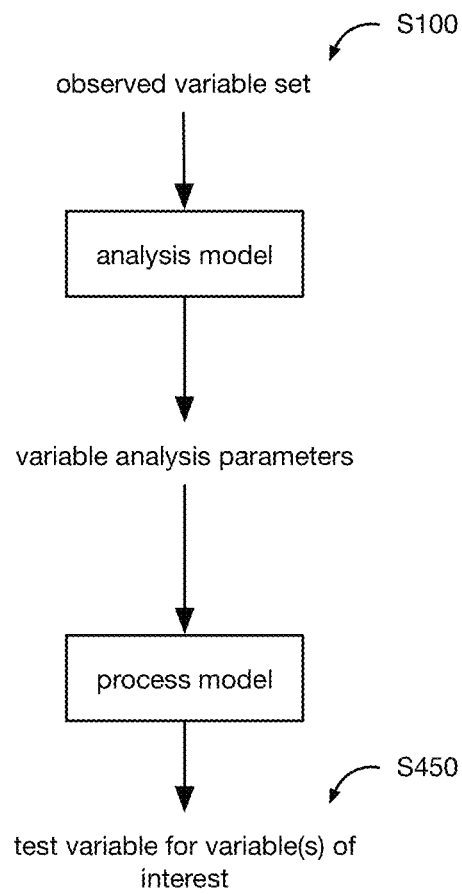
FIG. 9 depicts an example of determining a test variable using a process model.
Figure 10:
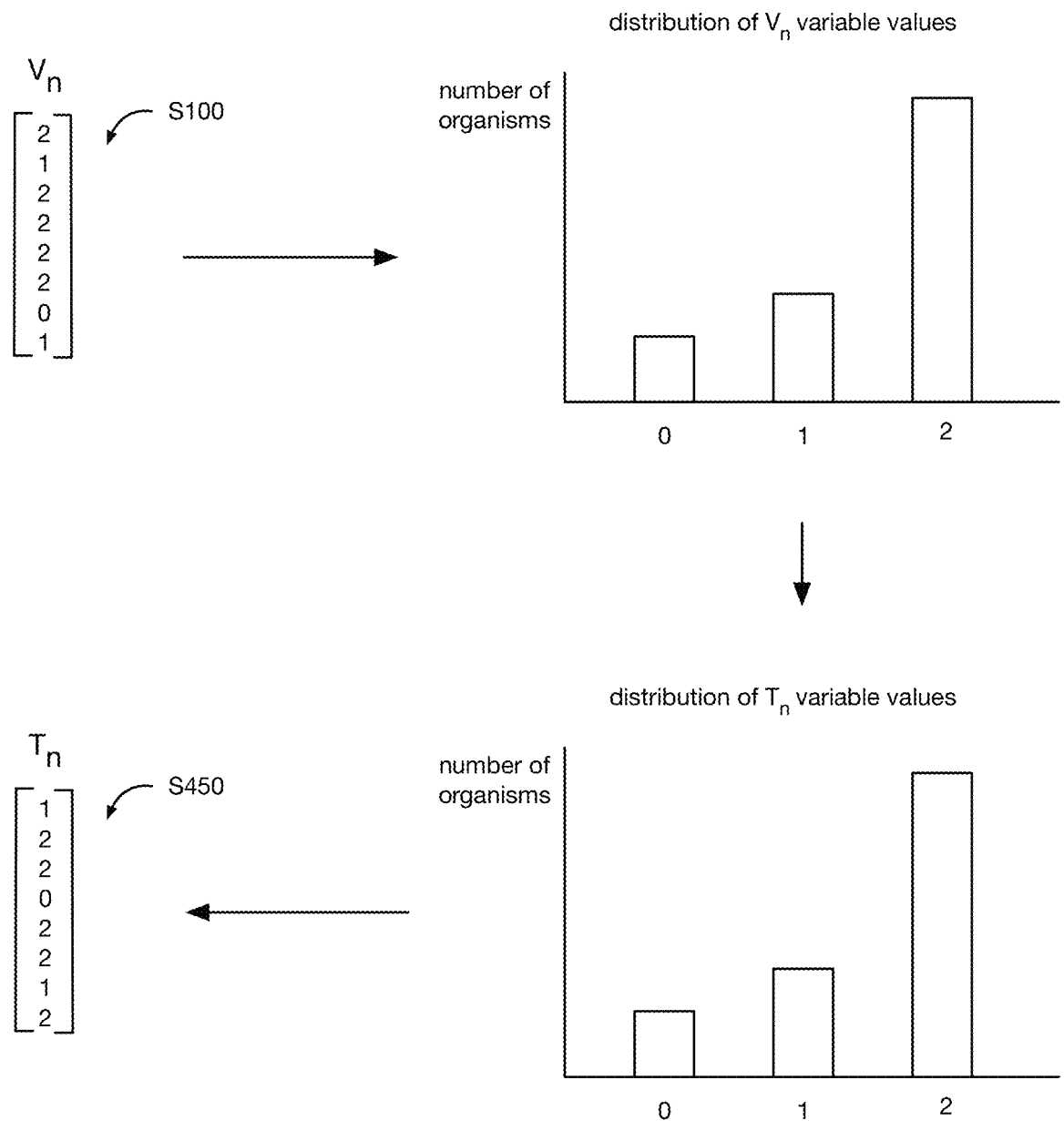
FIG. 10 depicts an example of determining a test variable using a variable value distribution.
Figure 12:
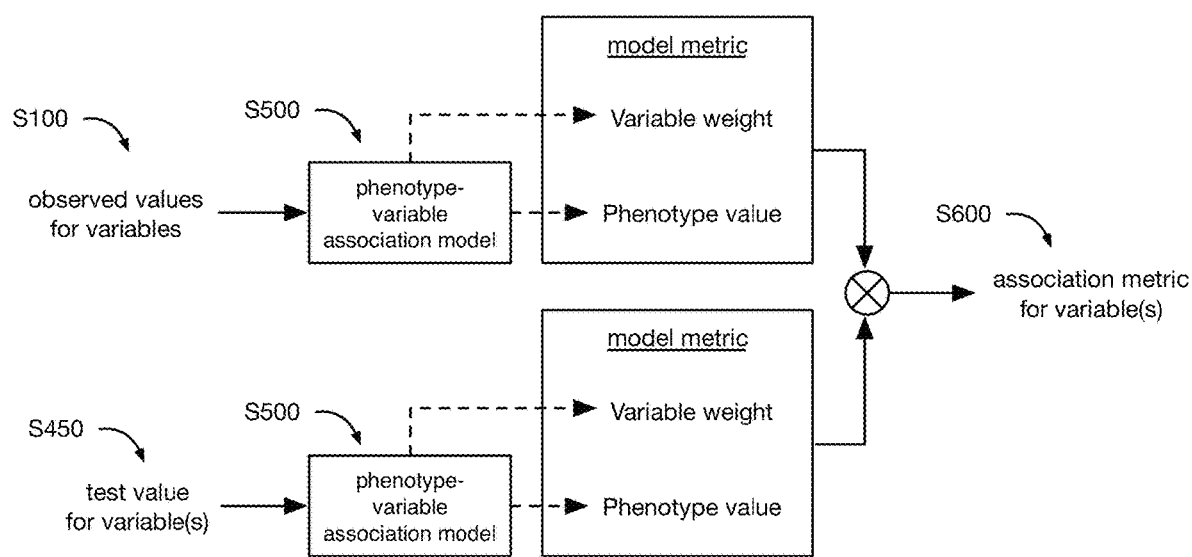
FIG. 12 depicts a first example of determining an association metric.

The test variable can be generated using a variable-variable association model, be randomly determined, be perturbed, be manually determined, and/or be otherwise determined. In a first variant, determining a test variable for a corresponding observed variable can include replacing the observed variable values with null values. In a second variant, determining a test variable can include randomly generating values to replace the observed variable values. In a third variant, determining a test variable can include adding noise to the observed variable values. In a fourth variant, determining a test variable can include determining a distribution of observed variable values based on the corresponding observed variable, and generating test variable values to match the distribution (e.g., a genotype distribution). For example, the distribution can be modeled (e.g., as a gaussian distribution), wherein test variable values can be randomly selected from the modeled distribution. An example is shown in FIG. 10. In a fifth variant, the test variable can be determined using a process model (e.g., representing how the variable values are generated). For example, the process model can be a forward-in-time evolution model. Inputs to the process model can include variable analysis parameters, other genetic parameters, and/or any other information. Outputs from the process model can include test variables (e.g., including synthetic variable values). An example is shown in FIG. 9. In a sixth variant, determining a test variable can include determining (e.g., training) a variable-variable association model, and determining the test variable using the variable-variable association model.

Inputs to the variable-variable association model can include: variable values (e.g., observed variables including observed variable values), an optional randomization parameter (e.g., a parameter that can introduce randomness in the model pre- or post-training), and/or any other suitable inputs. For example, observed variable inputs can include (only) the observed variables corresponding to the variable window. Outputs from the variable-variable association model can include: variable values (e.g., a test variable including test variable values), and/or any other suitable outputs. For example, test variable outputs can include a single test variable (associated with one or more observed variables) or multiple test variables (e.g., each associated with one or more observed variables).

Figure 6:
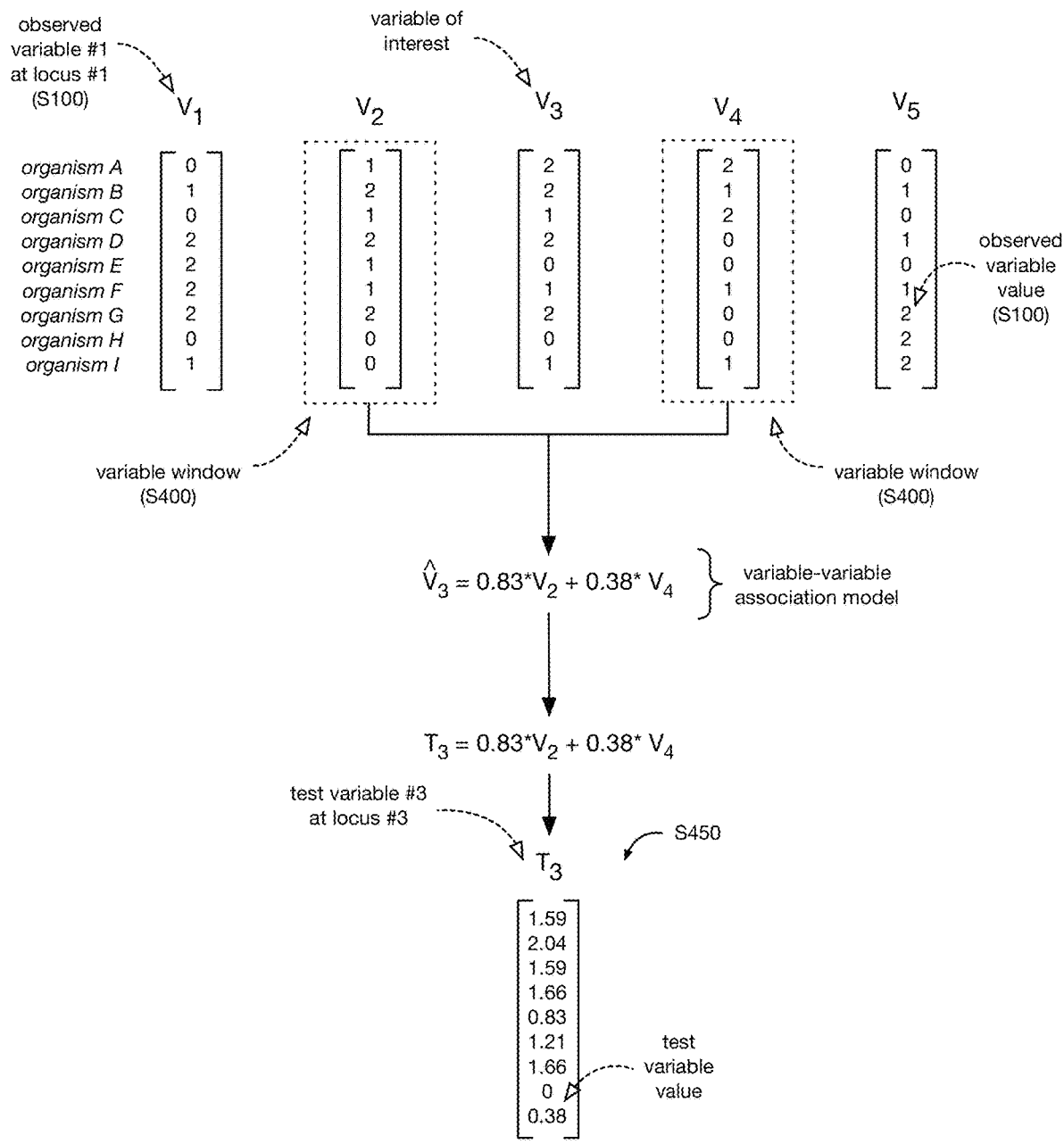
FIG. 6 depicts an example of test variable generation using a linear regression variable-variable association model.

In a first embodiment, the variable-variable association model includes a regression fit to observed variables, where the observed variable for the variable of interest is treated as the dependent variable and observed variables in the variable window are treated as the independent variables. The resulting (fitted) regression is then used to determine the test variable, wherein the test variable is treated as the dependent variable. An example is shown in FIG. 6.

In an illustrative example, the variable-variable association model is a regression of the form: $V_2 \sim a_1 V_1 + a_3 V_3$, where $V_2$ is the observed variable for variable 2 (e.g., locus 2), $V_1$ is the observed variable for variable 1, $V_3$ is the observed variable for variable 3 (e.g., where variable 1 and 3 are selected based on the variable window), and $a_1$ and $a_2$ are determined coefficients. The determined coefficients can be used to calculate the test variable for variable 2: $T_2 = a_1 V_1 + a_3 V_3$. For example, test variable T can include T values for each organism, calculated using the regression and the organism's observed values for $V_1$ and $V_3$.

Figure 7A:
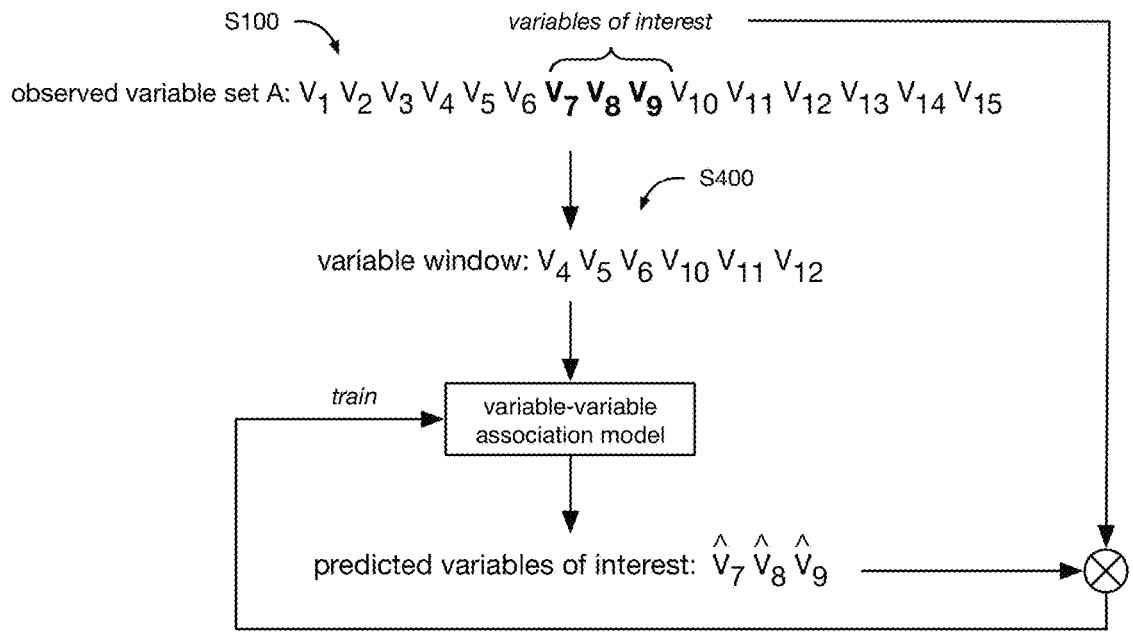
FIG. 7A depicts an example of training a variable-variable association model.
Figure 7B:
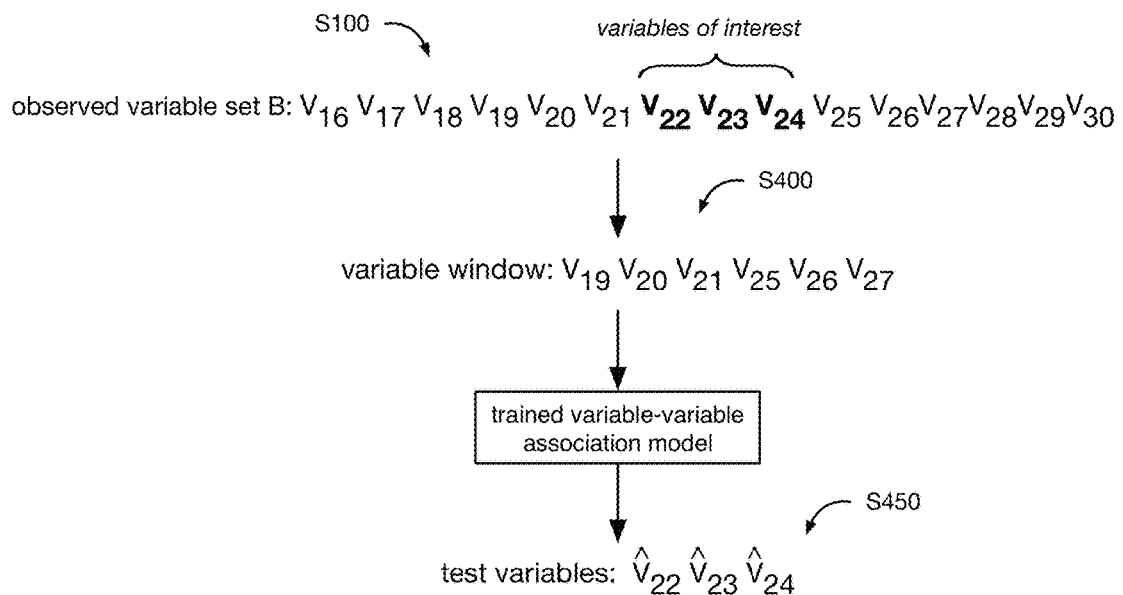
FIG. 7B depicts an example of determining a set of test variables using a trained variable-variable association model.

In a second embodiment, the variable-variable association model includes a machine learning model (e.g., an autoencoder, CNN, etc.) trained to predict test variable values based on the values for other observed variables. For example, the variable-variable association model can be trained on a first subset of variables (e.g., a first area of the genome), and then applied to a second subset of variables to determine test variables for variables of interest (e.g., outputting multiple test variables for multiple variables of interest). The first subset of variables can exclude the second subset of variables, include a portion of the second subset, be separated from the second subset by a threshold distance (e.g., genomic distance), or be otherwise related to the second subset of variables. In an example, the variable-variable association model can determine an encoding for the variables of interest (e.g., a single encoding for multiple variables of interest) based on observed variables in the variable window, wherein the encoding can be decoded to generate the individual test variables for the variables of interest. Examples of training and test variable value prediction is shown in FIG. 7A and FIG. 7B. In another example, the model can predict the loci values for the test variables based on the flanking (observed) loci values within the second subset of variables (e.g., using a deep learning network, a generative model, an autoencoder, etc.). In another example, the model can be a CNN trained to predict the phenotype value based on the variable values, wherein the CNN can implicitly learn the causal variables and/or features (e.g., intermediate variables). The causal variables can optionally be explicitly determined from the CNN (e.g., using explainability methods, such as SHAP values, lift, coefficient analysis, etc.), and/or not explicitly determined (e.g., wherein the CNN is used to determine the phenotype value as-is).

Figure 8:
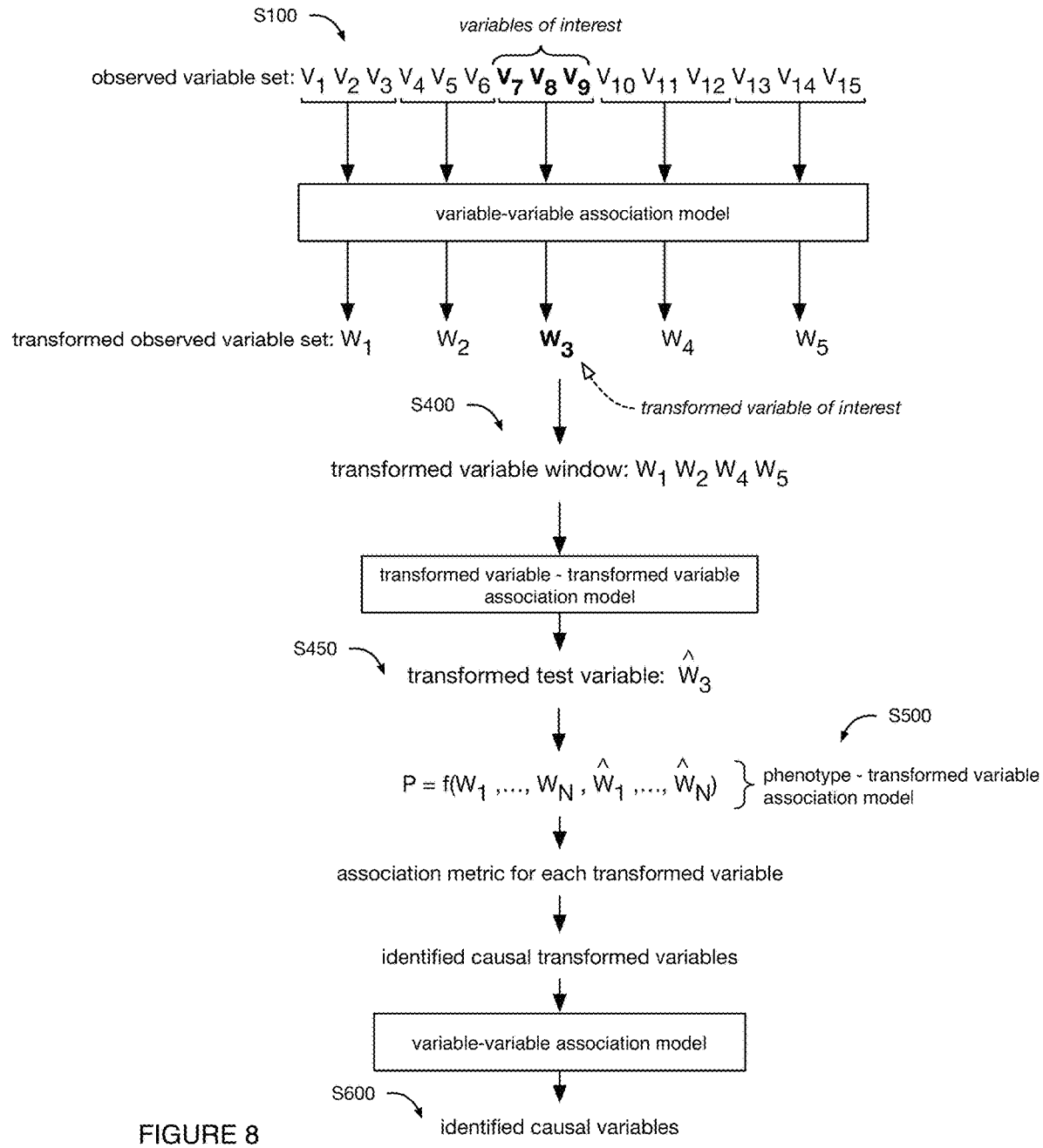
FIG. 8 depicts an example of determining a transformed test variable.

In a third embodiment, the variable-variable association model transforms variables to a reduced dimension space (e.g., latent space). For example, the variable-variable association model can compress (e.g., embed, reduce, etc.) the set of variables into a set of features, wherein the set of features is smaller than the set of variables (e.g., illustrative example shown in FIG. 8). Transformed observed variables (e.g., observed features) and transformed test variables (e.g., test features) can optionally be treated as observed variables and test variables, respectively, in all or parts of the method. For example, a phenotype-variable association model can include a relationship between a phenotype and transformed observed variables (e.g., the observed embedded variable, the observed feature, etc.) and/or transformed test variables (e.g., the test embedded variable, the test feature, etc.; wherein the test feature preserves the observed feature's distribution), wherein transformed causal variables (e.g., causal embedded variable, causal feature, etc.) can be identified using the phenotype-variable association model (e.g., using the features or embedded variables as the phenotype-variable association model's independent variables) and decoded (using the variable-variable association model) to determine the causal variables. An example is shown in FIG. 8.

In a first example, the variable-variable association model can be an autoencoder that is trained (e.g., trained using a different subset of variables than the subset associated with the variables of interest) to compress multiple observed variables into an encoding that can function as a transformed observed variable. In a second example, a first layer of a neural network (e.g., a phenotype-variable association model) can function as the variable-variable association model, wherein the first layer (e.g., a pooling layer) transforms observed variables into transformed observed variables. In a third example, principal component analysis and/or any other dimensionality reduction technique can be used to compress variables into transformed variables. A transformed test variable can optionally be determined based on the transformed observed variables. In examples, the transformed test variable can be determined: using a different variable-variable association model (e.g., including a relationship between transformed observed variables and the transformed test variable); by selecting (e.g., randomly selecting) transformed test values from a distribution of transformed observed values; and/or using any other test variable generation methods (e.g., as previously described).

In any embodiment, multiple instances of the variable-variable association model can optionally be determined (e.g., multiple instances separately trained, a single trained variable-variable association model with a different randomization parameter for each instance, etc.), wherein a test variable can be determined for the variable(s) of interest using each model instance.

Determining test variables can optionally include a test variable check, wherein a test variable does not pass if the test variable results in: a (substantial) deviation from the joint distribution between observed variables, a (substantial) deviation in the distribution of test values within the test variable relative to the distribution of observed values in the corresponding observed variable, and/or otherwise deviates from allowable criteria. Test variables that do not pass the test variable check can be adjusted, discarded, and/or otherwise processed.

The test variables can optionally be aggregated into a test data set (e.g., of the same form as the observed data set, of a modified form, etc.). In a first variant, the test data set contains test variables (e.g., with no observed variables) for each of the set of variables (e.g., the subset of variables). In a second variant, the test data set is the observed dataset with one or more observed variables replaced with the corresponding test variables (e.g., associated with the same variables). The observed variables that are replaced can be associated with variables of interest (e.g., variables to be tested for a phenotype association). In an example, the test data set can be the observed data set with a single observed variable exchanged with its corresponding test variable (e.g., when the set of target genomic components is a single genomic component). Examples are shown in FIG. 11B and FIG. 11C.

However, test variables can be otherwise determined.

Determining a phenotype-variable association model S500 functions to determine a model relating the phenotype to the set of variables (e.g., where the model predicts phenotype values given variable values). S500 can be performed after S300, before S300, after S100, after S200, and/or at any other time. The phenotype-variable association model can be determined: once (e.g., based on the observed data), multiple times (e.g., once for each variable of interest), and/or any other number of times.

The phenotype-variable association model can be: for a specific phenotype, for a phenotype set, and/or any other suitable combination of phenotypes. The phenotype-variable association model can be determined based on the observed values (e.g., from S100), based on test values (e.g., from S450), and/or based on any other set of data. The phenotype-variable association model preferably does not model inter-variable interactions, but alternatively can model inter-variable interactions. The phenotype-variable association model can be: selected, learned, fit, or otherwise determined. Inputs to the phenotype-variable association model can include: variable values (e.g., observed variables including observed variable values, test variables including test variable values, etc.) and/or any other suitable inputs. Outputs from the phenotype-variable association model can include: phenotype values (e.g., a phenotype including predicted observed phenotype values) and/or any other suitable outputs.

In a first variant, the phenotype-variable association model is a neural network trained to predict a phenotype (e.g., including a vector of phenotype values) based on the set of variables (e.g., including vectors of variable values). The phenotype-variable association model is preferably trained using observed variables and observed phenotypes for the population of organisms, but can additionally or alternatively be trained using any other phenotypes and/or variables.

In a second variant, the phenotype-variable association model is a regression. For example, S500 can include determining (e.g., calculating, fitting, etc.) a regression between a phenotype (e.g., the dependent variable) and variables (e.g., the independent variables). In this example, the variable values can include only observed variable values, only test variable values, and/or a combination of observed and test variable values. In a first example, S500 can include: determining an observed variable for each of the set of variables (e.g., S100), determining an observed phenotype (e.g., S100), and fitting the phenotype-variable association model based on the observed variables and the observed phenotype. In a second example, S500 can include: determining a test variable for each of the set of variables (e.g., S450), determining an observed phenotype (e.g., S100), and fitting the phenotype-variable association model based on the test variables and the observed phenotype. In a third example, S500 can include: determining an observed variable for each of the set of variables (e.g., S100), determining a test variable for the variables of interest and/or for each of the set of variables (e.g., S450), determining an observed phenotype (e.g., S100), and fitting the phenotype-variable association model based on the observed variables, the test variables, and the observed phenotype.

The phenotype-variable association model can use the variable values for: all variable types (e.g., genomic component, DNA methylation, gene expression, environmental variables, transcriptome variables, etc.), a subset of variable types (e.g., only genomic component, only genomic component and gene expression, etc.), and/or any other combination of variable types. In a first example, the model predicts a value for a single phenotype based on values for a set of genomic component variables (e.g., genotypes). In a second example, the model predicts a value for a first phenotype and a value for a second phenotype based on values for genomic component variables, environmental variables, gene expression variables, and/or DNA methylation variables. In a third example, a first instance of the model predicts a phenotype value based on values for a set of genomic component variables, a second instance of the model predicts a phenotype value (e.g., for the same phenotype) based on values for a set of environmental variables, and a third instance of the model predicts a phenotype value based on values for a set of gene expression variables.

However, the phenotype-variable association model can be otherwise determined.

Identifying causal variables associated with a phenotype S600 functions to reduce the variable dimensionality and/or identify variables that influence trait expression. S600 can be performed after S300, after S500, and/or at any other time.

Causal variables can be a subset of the set of variables, wherein a set of causal variables can be selected for: a set of phenotypes (e.g., target phenotypes), an individual phenotype, and/or can be otherwise selected. The causal variables can be selected based on observed variables, test variables, and observed phenotypes (e.g., observed variable values, test variable values, and observed phenotype values for each organism in a population). However, the causal variable can be selected based on any other variable values and/or phenotype values.

The causal variables can be selected from the set of variables: manually, using a phenotype-variable association model, randomly, and/or otherwise selected. Selecting the causal variables using a phenotype-variable association model can include: determining an association metric for each variable based on the phenotype-variable association model; and selecting the causal variables from the set of variables based on the respective association metric for each variable.

Determining an association metric for each variable based on the first model can function to extract information on the relationship between each variable and one or more phenotypes. Association metrics for different variables can be independently determined or, alternatively, can be concurrently determined. Multiple variables can optionally be associated with the same association metric (e.g., example shown in FIG. 17).

Determining the association metric for a variable of interest preferably includes determining a model metric for the phenotype-variable association model with and without the information for the variable of interest (e.g., an observed model metric and a test model metric, respectively), and determining the association metric based on a comparison between the model metrics. The comparison can include a difference, a ratio, a statistical measure, a distance metric, an aggregate of comparisons, an absolute value thereof, and/or any other comparison. Examples of model metrics include: the variable weight (e.g., a coefficient in the model), the model's phenotype prediction, the model's loss, the model's variance (e.g., coefficient of determination), a model fit metric (e.g., R-squared, RMSE, etc.), log-likelihood evaluation, a variable classification (e.g., causal or non-causal variable), a model classification (e.g., predictive or non-predictive), statistical measure, summary statistics, and/or any other value determined based on the phenotype-variable association model. Examples are shown in FIG. 12, FIG. 13, FIG. 14, FIG. 15, FIG. 20, and FIG. 21. Alternatively, the association metric can be determined based on a single model metric value (e.g., a measure of association between the variable of interest and a phenotype). In an illustrative example, the association metric can be a coefficient for the variable of interest in the phenotype-variable association model (e.g., where test variable values are not used in the model).

Figure 17:
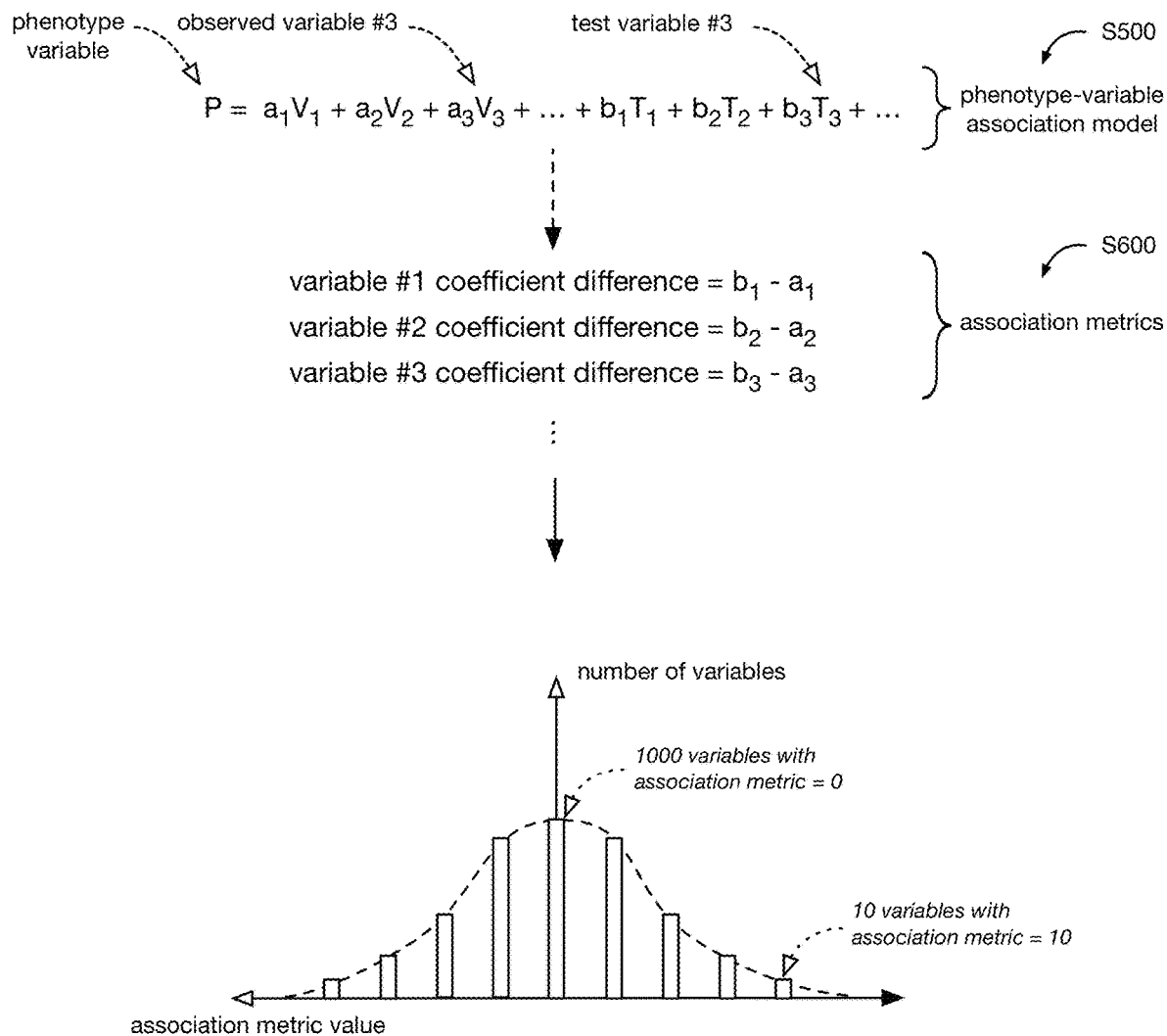
FIG. 17 depicts an illustrative example of association metrics.

In a first example, a single instance of the phenotype-variable association model is used to determine the observed model metric and test model metric. In a specific example, the phenotype-variable association model includes both a test variable for the variable of interest and an observed variable for the variable of interest (e.g., includes a single test variable for the variable of interest and an observed variable for each of the set of variables; includes a test variable and an observed variable for each of the set of variables; etc.), wherein a test model metric (e.g., a variable weight) can be determined for the test variable and an observed model metric can be determined for the observed variable. The association metric can be determined based on a comparison between the test model metric and the observed model metric. An example is shown in FIG. 17.

Figure 13:
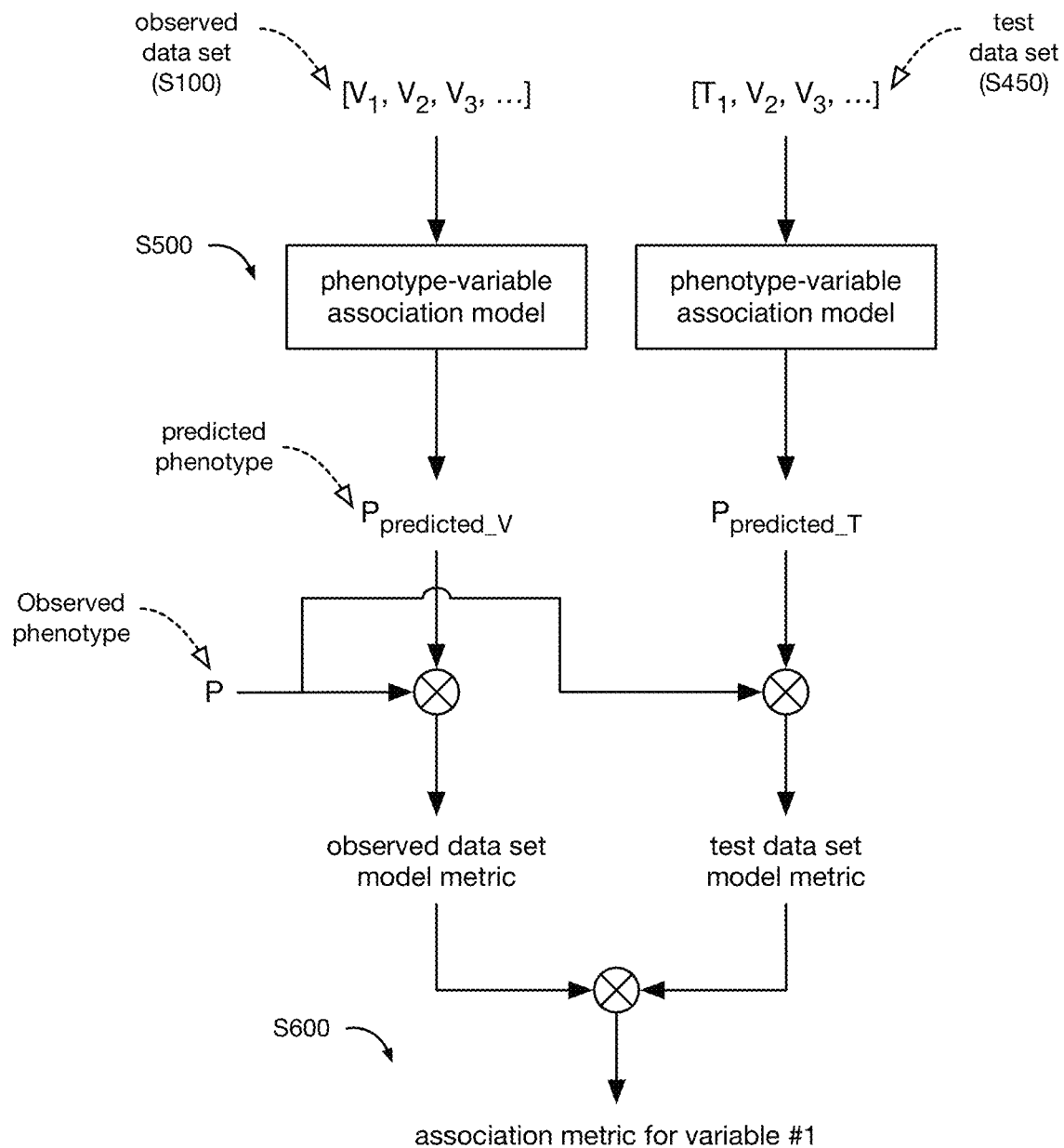
FIG. 13 depicts a second example of determining an association metric.
Figure 14:
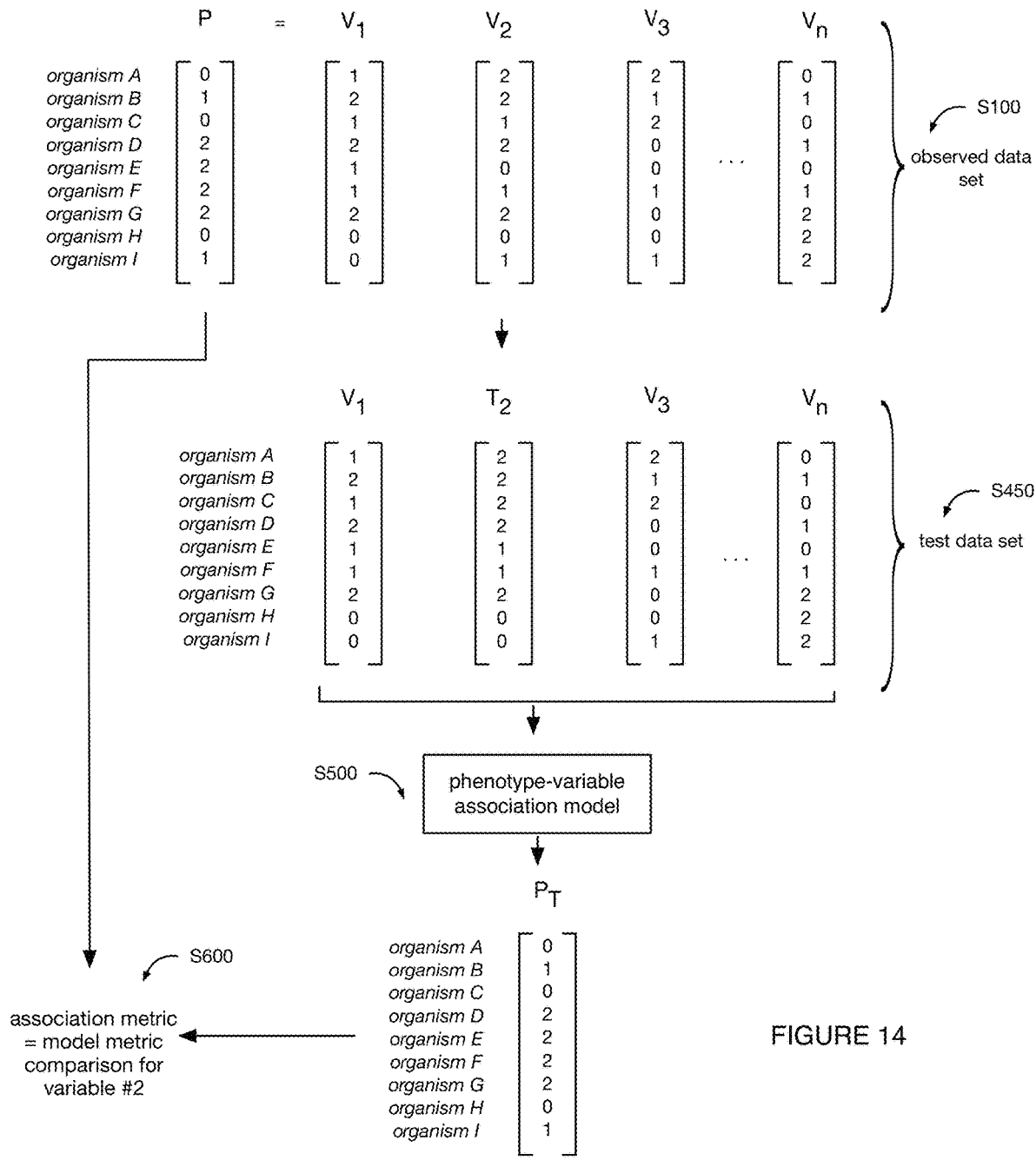
FIG. 14 depicts a third example of determining an association metric.
Figure 15:
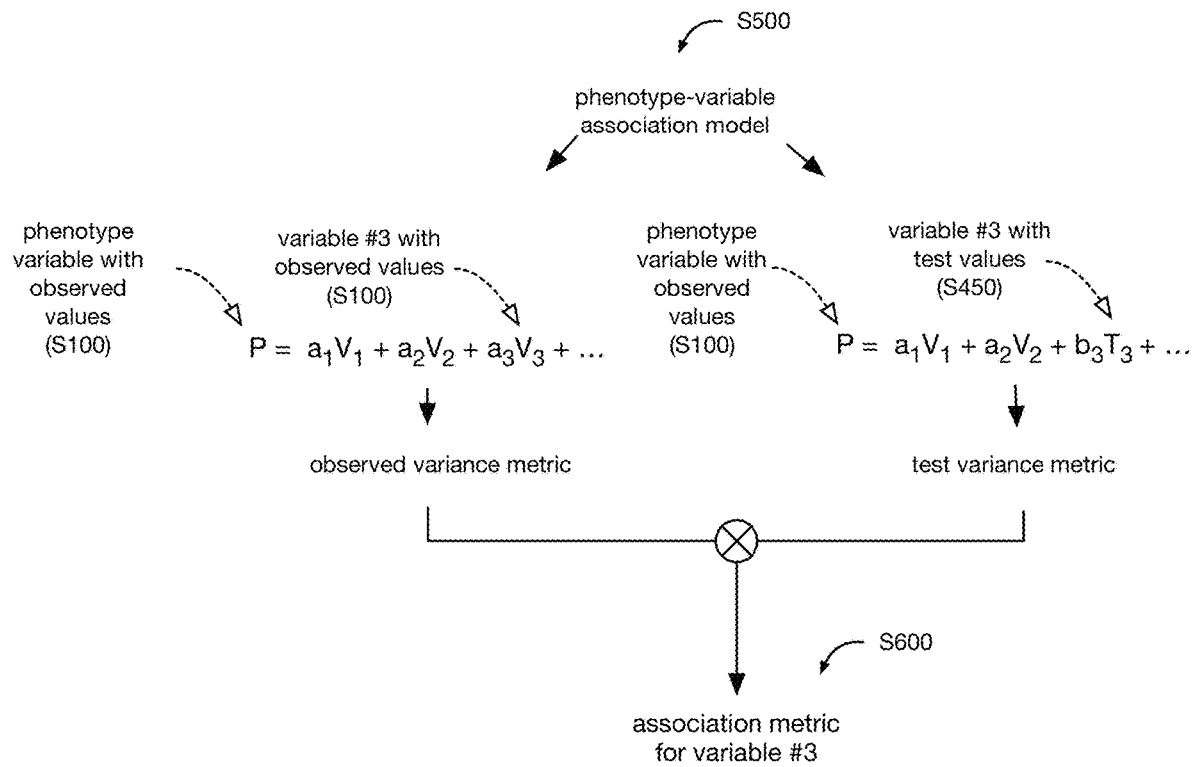
FIG. 15 depicts a fourth example of determining an association metric.

In a second example, two instances of the phenotype-variable association model are used to determine the observed model metric and test model metric. In a specific example, a test phenotype-variable association model includes a test variable for the variable of interest and an observed phenotype-variable association model includes an observed variable for the variable of interest (e.g., includes only observed variables for each of the set of variables), wherein a test model metric (e.g., a variable weight, a model loss, etc.) can be determined based on the test phenotype-variable association model an observed model metric can be determined based on the observed phenotype-variable association model. The association metric can be determined based on a comparison between the test model metric and the observed model metric. In examples, the test phenotype-variable association model can include, in addition to the test variable for the variable of interest: observed variables for all or a subset of the set of variables (e.g., the entire set of variables except the variable of interest); test variables for each of the set of variables (e.g., without observed variables); and/or include any other combination of observed and/or test variables. An example is shown in FIG. 13 and FIG. 15.

Figure 16:
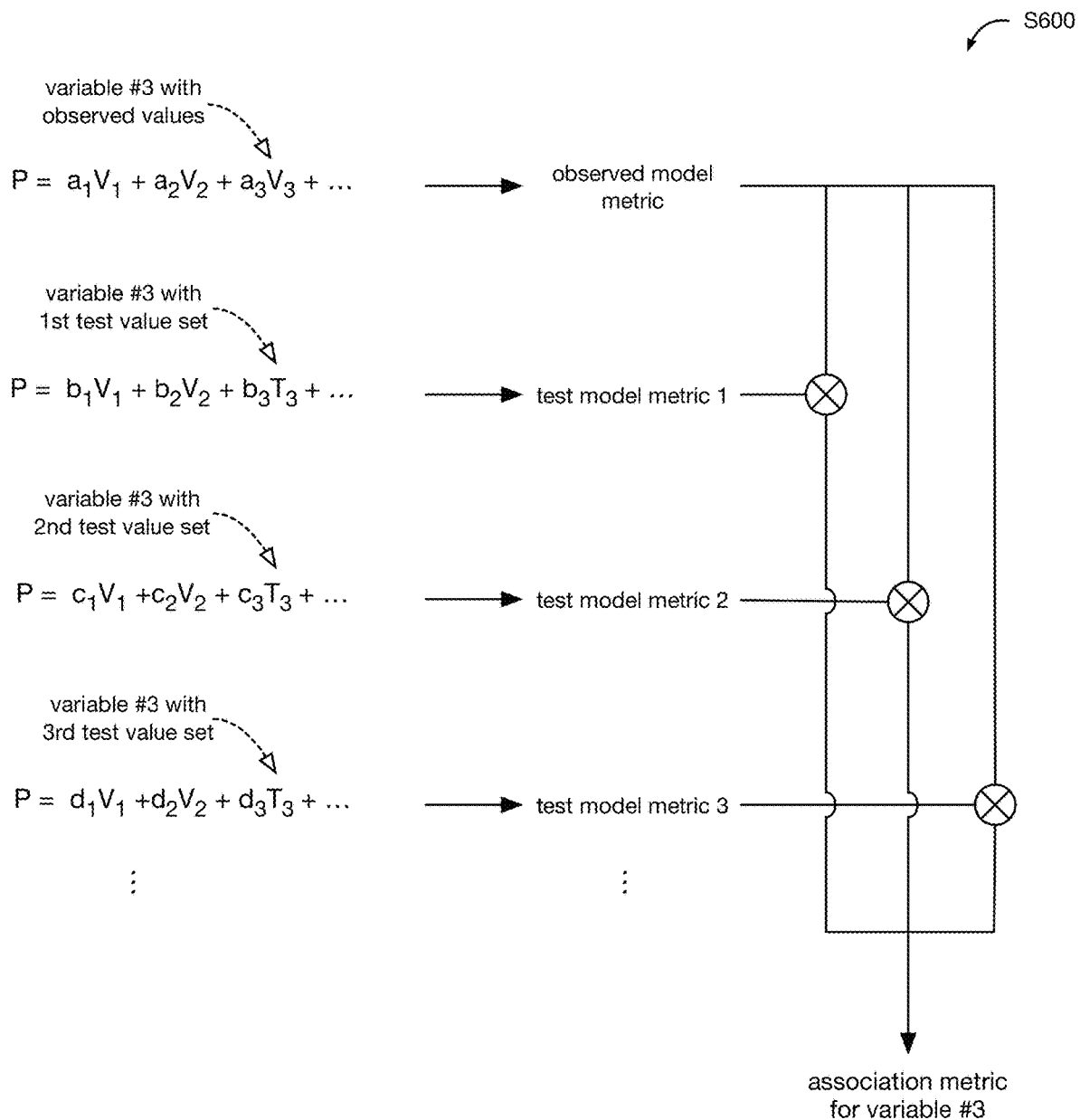
FIG. 16 depicts an example of determining an association metric for a variable based on multiple test model metrics for the variable.

In a third example, more than two instances of the phenotype-variable association model are used to determine the observed model metric and test model metric. In a specific example, an observed phenotype-variable association model includes an observed variable for the variable of interest (e.g., includes only observed variables for each of the set of variables), and each of a set of test phenotype-variable association models includes a test variable instance for the variable of interest. An observed model metric (e.g., a variable weight, a model loss, etc.) can be determined based on the observed phenotype-variable association model, and a test model metric can be determined for each test phenotype-variable association model, wherein the association metric can be based on an aggregate of comparisons between the observed model metric and each test model metric. In an illustrative example, each comparison includes a binary value (e.g., 0 corresponds to a test model metric greater than or equal to the observed model metric; 1 corresponds to a test model metric less than the observed model metric), wherein the aggregate of comparisons (e.g., average) represents a statistical measure (e.g., p-value, probability, etc.) that the test model metric is greater than the observed model metric. An example is shown in FIG. 16.

Figure 20:
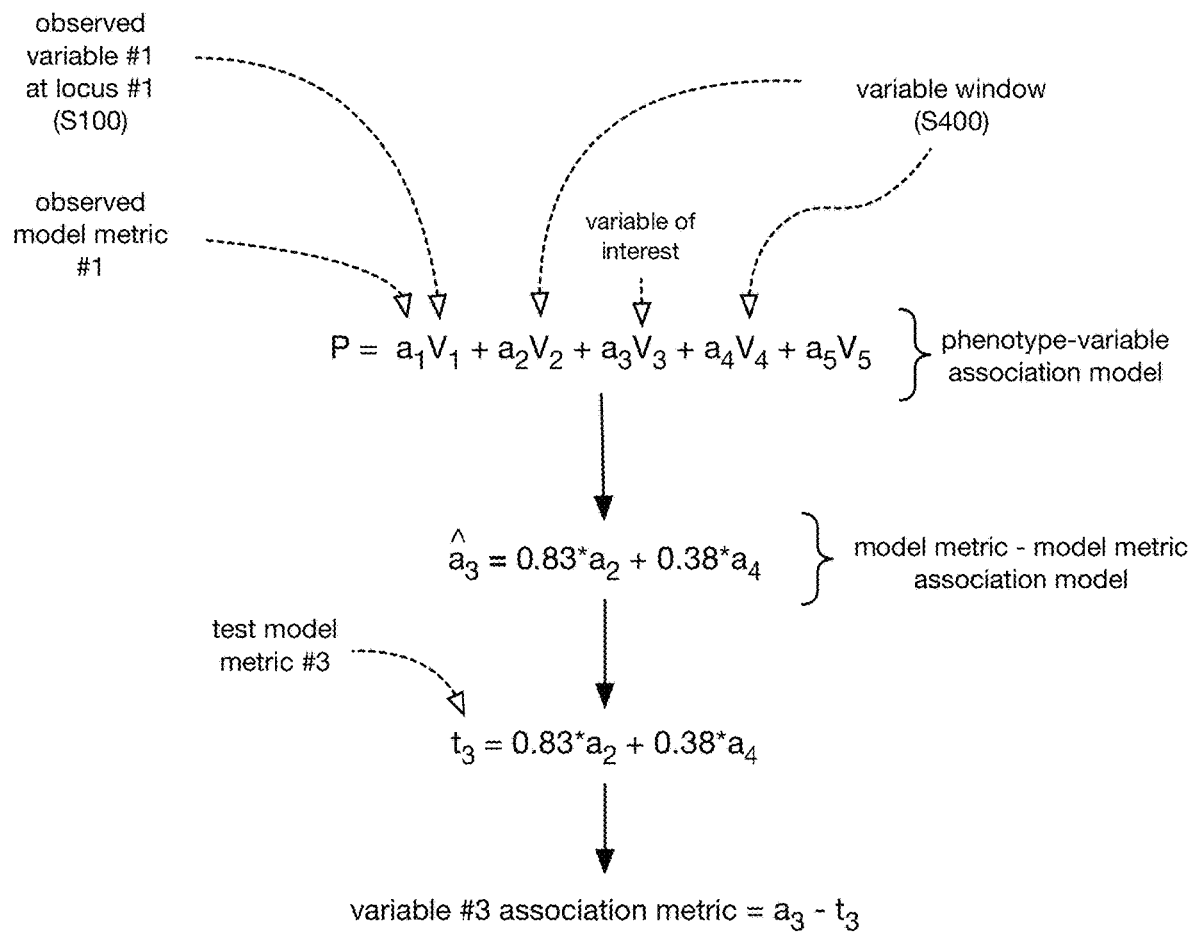
FIGS. 20 and 21 depict a first and second variant of determining a test summary statistic.
Figure 21:
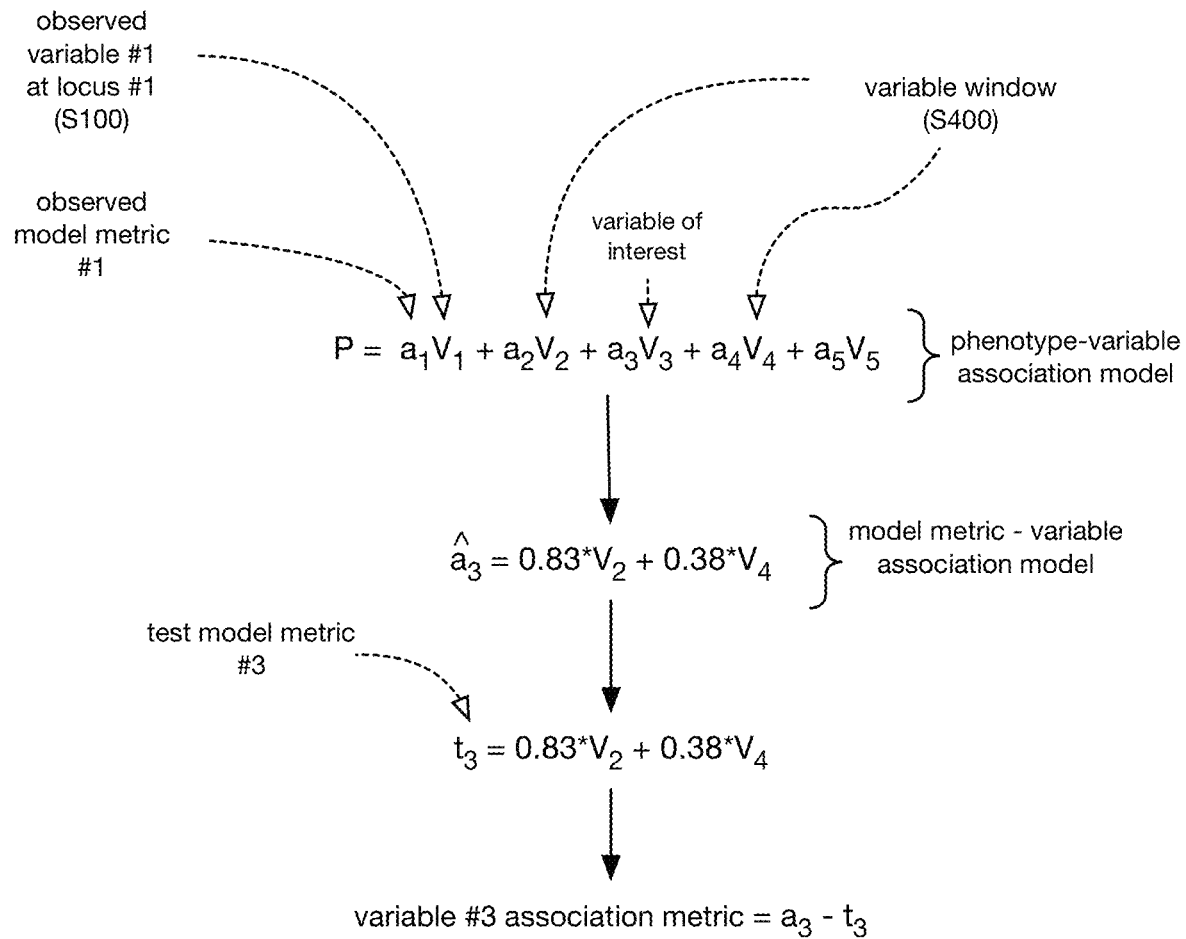

In a fourth example, the association metric can be determined based on a test summary statistic (e.g., for the variable of interest). The test summary statistic can be determined based on the neighboring summary statistics (e.g., for variables in the variable window), based on the neighboring variable values (e.g., for the variables in the variable window), and/or based on any other suitable information. Test summary statistics can be generated in the same and/or similar manner as generating test variables, and/or otherwise determined. In a first specific example, this can include: fitting an observed phenotype-variable association model using observed values; fitting a metric-variable association model that treats the summary statistic of the variable of interest (e.g., the variable of interest's weight from the observed phenotype-variable association model) as the dependent variable and the summary statistics of the neighboring variables as the independent variables; and determining the test summary statistic based on the metric-variable association model (e.g., by calculating the test summary statistic value using the neighboring summary statistics, by calculating the test summary statistic value without using observed variable values; by calculating the test summary statistic value using the observed neighboring variable values; etc.). An example is shown in FIG. 20. In a second specific example, this can include: fitting an observed phenotype-variable association model using observed values; fitting a metric-variable association model that treats the summary statistic of the variable of interest (e.g., the variable of interest's weight from the observed phenotype-variable association model) as the dependent variable and the neighboring variables as the independent variables; and determining the test summary statistic based on the metric-variable association model (e.g., by calculating the test summary statistic value using the observed neighboring variable values, etc.). An example is shown in FIG. 21. In a first variant, association metrics are determined using a phenotype-variable association model that includes a regression.

In a first embodiment, determining association metrics using a regression includes calculating a regression based on the observed variables and their corresponding test variables:

$$P \sim a_1 V_1 + a_2 V_2 + \ldots + a_n V_n + b_1 T_1 + b_2 T_2 + \ldots + b_n T_n$$

where P is the observed phenotype variable, $V_i$ is the observed variable for variable i, $T_i$ is the test variable for variable i, and $a_i$ and $b_i$ are the observed and test coefficients for the observed and test variables for variable i, respectively. In this embodiment, the coefficients are the model metrics (e.g., the observed and test coefficients are the observed and test model metrics, respectively), wherein the comparison between the coefficients is the association metric used to identify the causal variables associated with the phenotype. In an example, the difference between the observed and test coefficients for each variable (e.g., $a_n - b_n$) is the association metric for the respective variable.

In a second embodiment, determining association metrics using a regression includes: calculating individual regressions for each variable (x) from a set of variables (1 to n):

$$P \sim a_1 V_1 + \ldots + a_x T_x + \ldots + a_n V_n$$

where P is the observed phenotype variable, $V_i$ is the observed variable for variable i, $T_x$ is the test variable for variable x, and $a_i$ is the coefficient for the variable for variable i. In an example, the variation (e.g., $R^2$) for the regressions can be used as the model metric. In a specific example, the observed variation (e.g., $R^2$) for the observed regression (e.g., from S200) and the test variation (e.g., $R^2_T$) from each individual regression can be calculated and compared to determine the association metric for each variable.

However, regression-based phenotype-variable association models can be otherwise used to determine association metrics.

In a second variant, association metrics are determined using a phenotype-variable association model that includes a machine learning model (e.g., a neural network, Bayesian model, SVM, etc.).

In a first embodiment, determining association metrics using a machine learning model includes: training an observed phenotype-variable association model to predict the observed phenotype values based on the observed variable values; constructing a test data set having test values (e.g., determined in S450) for one or more variables of interest; and training a test phenotype-variable association model to predict the observed phenotype values based on the test data set. The observed and test phenotype-variable association model preferably have the same base model but can alternatively have different base models. In an example, a model performance metric (e.g., loss, accuracy, etc.) can be used as the model metric, wherein the association metric for the variable(s) of interest can be a comparison between the model metric for the observed phenotype-variable association model and the model metric for the test phenotype-variable association model.

In a second embodiment, determining association metrics using a machine learning model includes: training a phenotype-variable association model to predict the observed phenotype(s) based on the observed variables; generating test variables by replacing the observed variable value for each organism's genotype with a test value (e.g., S450); predicting the phenotype value using the test variables (e.g., replacing one or more observed variables with test variables as inputs to the phenotype-variable-association model); and calculating the model performance for the prediction. In an example, a model performance metric can be used as the model metric, wherein the association metric can be determined based on a comparison between model performance using (only) the observed variables, and model performance when one or more observed variables are replaced with test variables.

In a third embodiment, determining association metrics using a machine learning model includes training a model to predict the phenotype values using the observed variable values; treating each variable as a feature, and using feature selection and/or explainability methods (e.g., local interpretable model-agnostic explanations, Shapley Additive explanations, partial dependence plots, etc.) to determine the association metrics (e.g., indicating how influential a variable is).

However, association metrics can be otherwise determined.

Figure 18A:
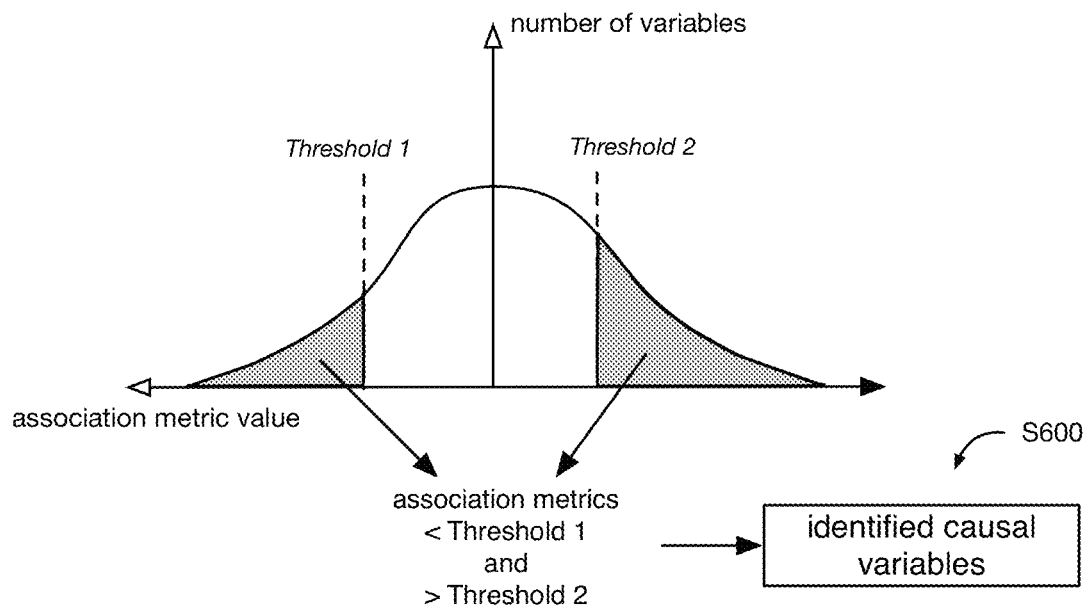
FIGS. 18A and 18B depict illustrative examples of identifying casual variables.
Figure 18B:
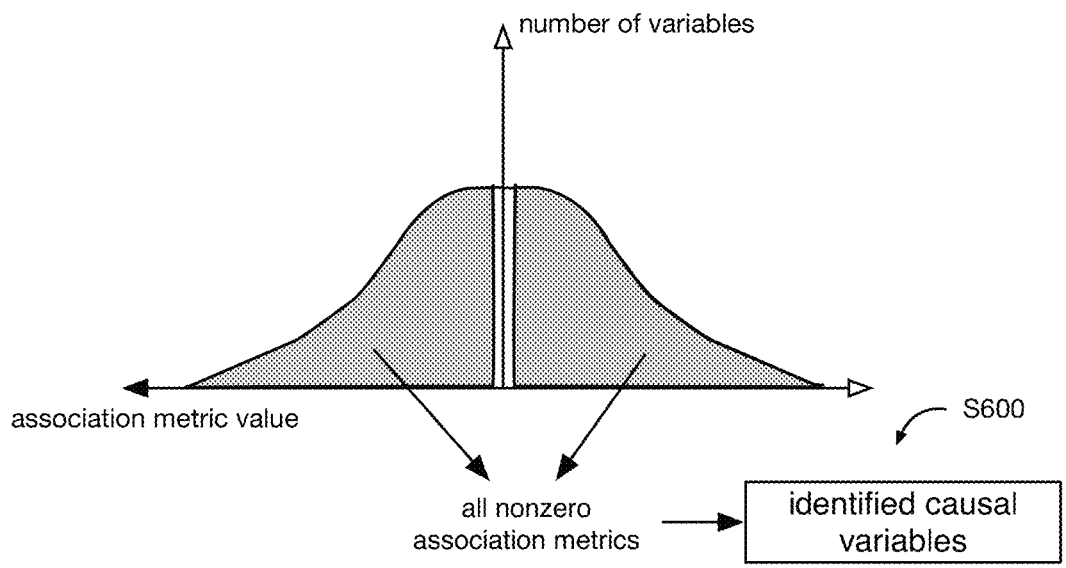

Selecting the causal variables from the set of variables based on the respective association metric for each variable can include selecting: variables with nonzero (e.g., positive and negative; valence agnostic) association metrics, variables with association metrics satisfying a threshold condition (e.g., absolute value above or below a threshold; above a first positive threshold or below a second (negative) threshold; etc.), a predetermined number and/or percent of variables with the largest positive association metric values, a predetermined number and/or percent of variables with the largest negative association metric values, a predetermined number and/or percent of variables with the largest absolute association metric values, variables with association metrics satisfying a statistical measure condition (e.g., variables with association metrics that are outliers, variables with association metrics that are at least a threshold standard deviation above/below the mean, etc.), a combination thereof, and/or any other variable subset. In a first example, the variables can be ranked based on their association metrics, wherein the selected causal variables can be the top m variables. In a specific example, m can be between 1-10,000 or any range or value therebetween (e.g., 10-1,000), but can alternatively be less than 1 or greater than 10,000. In a second example, the variables can be ranked based on their association metrics, wherein the selected causal variables can be the variables n standard deviations from the mean. In a specific example, n can be between 1-5 or any range or value therebetween (e.g., 2, 3, 4, etc.), but can alternatively be less than 1 or greater than 5. Examples are shown in FIG. 18A and FIG. 18B. In a third example, variables with the top percentiles of association metric values (e.g., top 20%, 15%, 10%, 5%, 2%, etc. of variables) can be selected as the causal variables. The association metric value can be valence agnostic, or account for valence. Additionally or alternatively, all variables of a specific type and/or classification can be selected (e.g., all environmental variables). However, causal variables can be otherwise selected form the set of variables.

Figure 19:
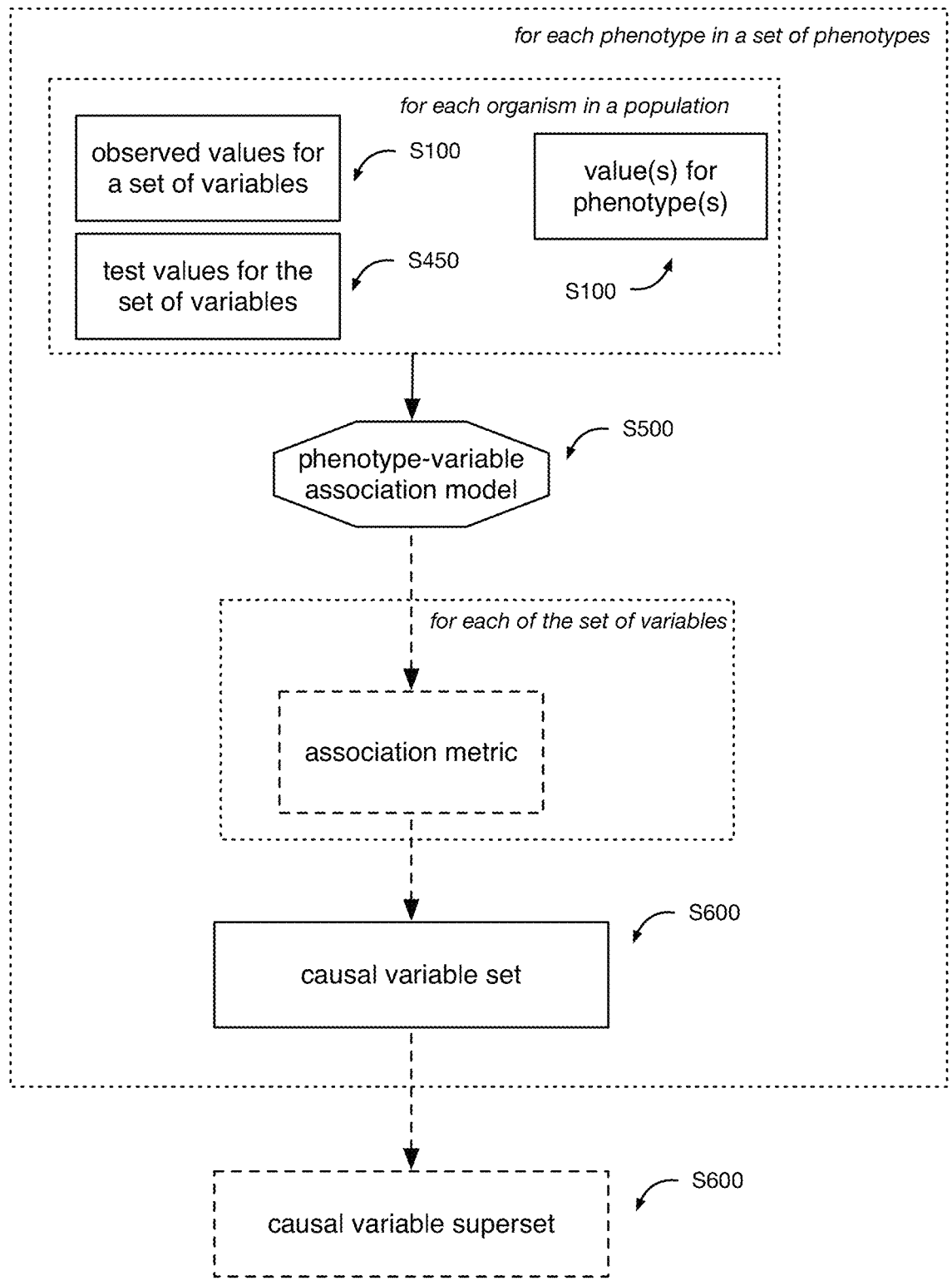
FIG. 19 depicts an example of identifying causal variables.

The causal variables can optionally be a superset of multiple causal variable sets. For example, S600 can be repeated with a different model for each phenotype in a set, wherein different causal variable sets are selected for each phenotype and then aggregated to generate a superset of causal variables (e.g., example shown in FIG. 19).

However, causal variables can be otherwise identified.

The method can optionally include determining breeding parameters to achieve a target causal variable value set S700, which functions to determine an organism that will exhibit a target phenotype. The organism can subsequently be bred using the breeding parameters; however, the breeding parameters can be otherwise used. All and/or portions of S700 can be performed after S600, S710 independent of S100-S600, before and/or after any of S100-S600, and/or at any other time. S700 or components thereof can be performed: once, iteratively until a stop condition is met (e.g., for a predetermined number of iterations, until a marginal improvement in the predicted phenotype value set falls below a threshold for predetermined number of iterations, until the predicted phenotype value matches the target phenotype value, etc.), and/or any number of times.

Figure 22:
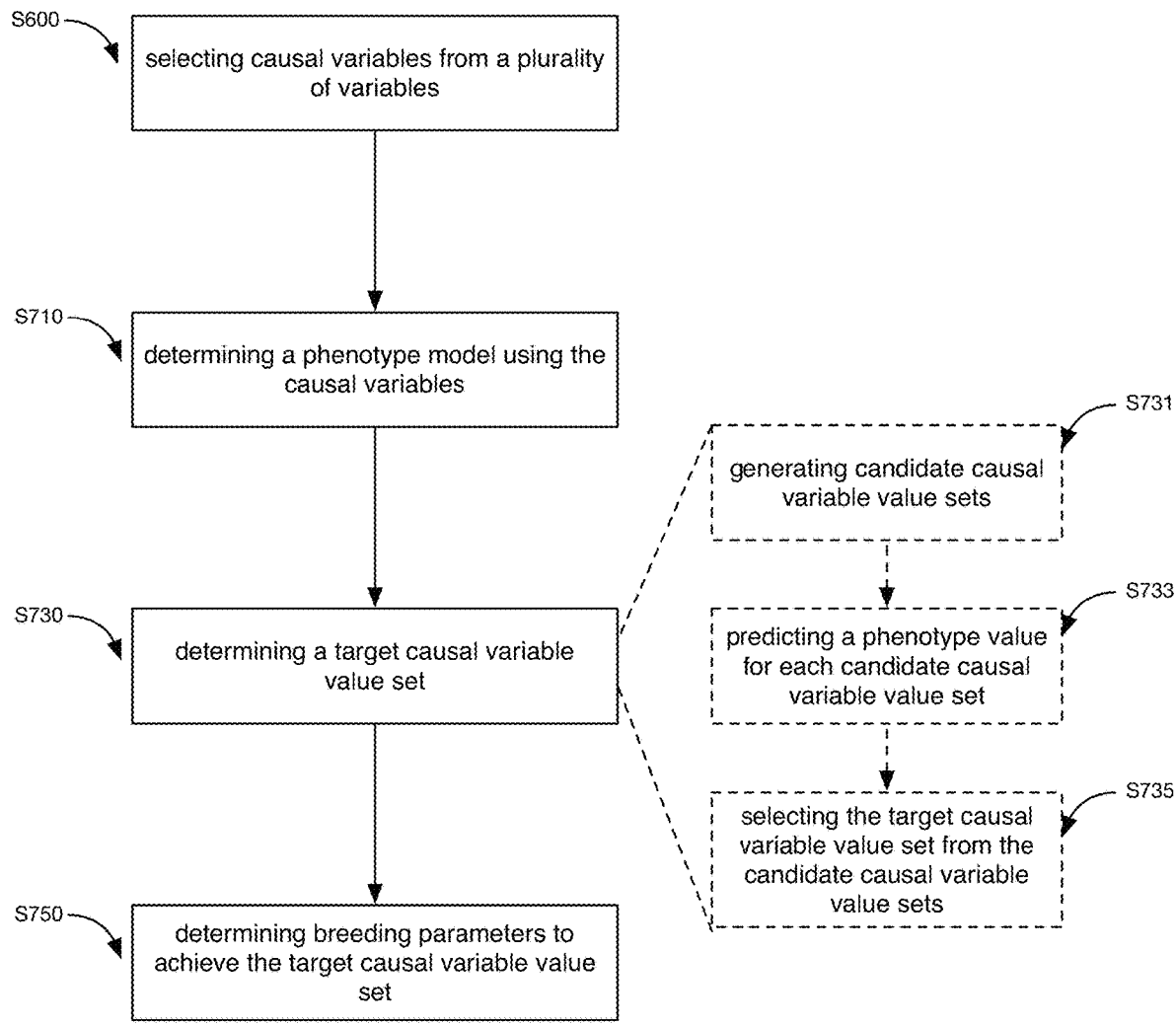
FIG. 22 is a schematic representation of a variant of the method for determining a set of breeding parameters.

As shown in FIG. 22, determining breeding parameters S700 can include: determining a phenotype model using the causal variables S710 (selected in S600), optionally determining a target causal variable value set S730, and determining breeding parameters to achieve the target causal variable value set S750. Alternatively, the breeding parameters can be determined experimentally (e.g., by growing the organisms, etc.), and/or be otherwise determined.

Determining a phenotype model using the causal variables S710 functions to determine an phenotype model (e.g., updated phenotype-variable association model) with a reduced number of variable inputs relative to the phenotype-variable association model used for causal variable selection (in S600). S710 can be performed after S600 and/or any other time. S710 or components thereof can be performed: once, iteratively until a stop condition is met (e.g., for a predetermined number of iterations, until a marginal improvement in the predicted phenotype value set falls below a threshold for predetermined number of iterations, until the predicted phenotype value matches the target phenotype value, etc.). A different phenotype model is preferably determined for each phenotype set (e.g., trait, trait value, etc.); alternatively a phenotype model for one phenotype set can be used for other phenotype sets.

The causal variables can be determined using one or more of S100-S600, be manually determined, be predicted, be learned (e.g., by a neural network, trained to predict a set of phenotype values based on a set of variable values), be randomly selected, and/or be otherwise determined.

The phenotype model is preferably a model trained to determine (e.g., predict) one or more phenotype values for an organism, given the organism's causal variable values. The phenotype model is preferably the same model class as the phenotype-variable association model used in S600, but can alternatively be a different model class (e.g., a low-dimension version) and/or otherwise configured. The phenotype model can be and/or include: a regression, support vector machine, classifier, random forest, kernel methods, generative model, clustering model, Bayesian model (e.g., HMM), neural network (e.g., CNNs, DNNs, etc.), equation, probability, deterministics, genetic program, generative model, and/or any model that could fit the biology. The phenotype model can be a linear model, nonlinear model (e.g., regression, neural network), and/or other model. The phenotype model can be learned (e.g., using supervised learning, unsupervised learning, etc.), fit, trained, predetermined, and/or can be otherwise determined.

The phenotype model can be determined (e.g., trained) based on one or more phenotypes and one or more causal variables (e.g., one phenotype value and one set of causal variable values for each of a set of organisms). Phenotype values and causal variable values are preferably observed (e.g., experimentally derived values, the same values as those determined in S100, etc.), but can alternatively be synthetic values (e.g., to simulate variables outside an observed variable distribution). The phenotype model can include more, less, or the same variable types as the phenotype-variable association model used in S600. The phenotype model preferably models inter-variable interactions, but alternatively can ignore inter-variable interactions.

In a first variant, the phenotype model is a neural network trained to predict phenotype values (e.g., trait values) given known values (e.g., observed values, predicted values, etc.) for the causal variables for one or more organisms.

In a second variant, the phenotype model is a regression fit to the observed phenotype values and the observed causal variable values, wherein the phenotype values are treated as the dependent variables and the causal variable values are treated as the independent variables.

In a third variant, the phenotype model is a machine learning model (e.g., neural network) trained to predict the phenotype value(s) based on the parent organisms' variable values (e.g., the parent organisms' causal variable values).

In a first example, the phenotype model predicts a value for a single phenotype based on values for causal genomic component variables (e.g., genotypes), causal environmental variables, causal gene expression variables, and causal DNA methylation variables. In this example, the set of causal variables (determined in S600) includes causal genomic component variables, causal environmental variables, causal gene expression variables, and causal DNA methylation variables.

In a second example, the phenotype model predicts a value for a plurality of phenotypes (e.g., trait values), wherein the phenotype model's variables can be determined from the causal variables for each of the respective phenotypes (e.g., include all causal variables for all of the phenotypes, the intersection of the causal variable sets, any other suitable combination of the respective causal variable sets, etc.). The causal variables for each phenotype is preferably independently determined (e.g., using different instances of S100-S600; using different phenotype-variable association models; etc.), but can alternatively be determined together (e.g., using the same instance of S100-S600; using the same phenotype-variable association model; etc.). For example, the causal variables can be a superset of multiple causal variable sets. In this example, S600 can be repeated with a different model for each phenotype in a set, wherein different causal variable sets are selected for each phenotype and then aggregated to generate a superset of causal variables (e.g., example shown in FIG. 19).

Figure 23A:
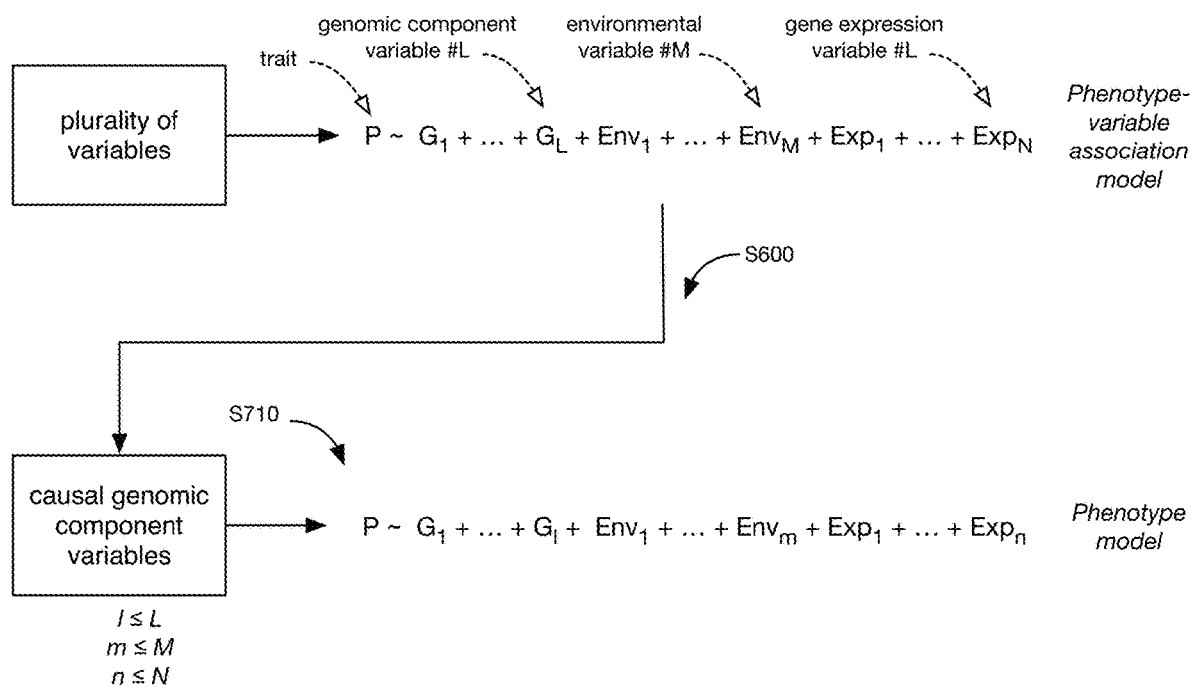
FIGS. 23A, 23B, and 23C depict examples of determining a phenotype model.
Figure 23B:
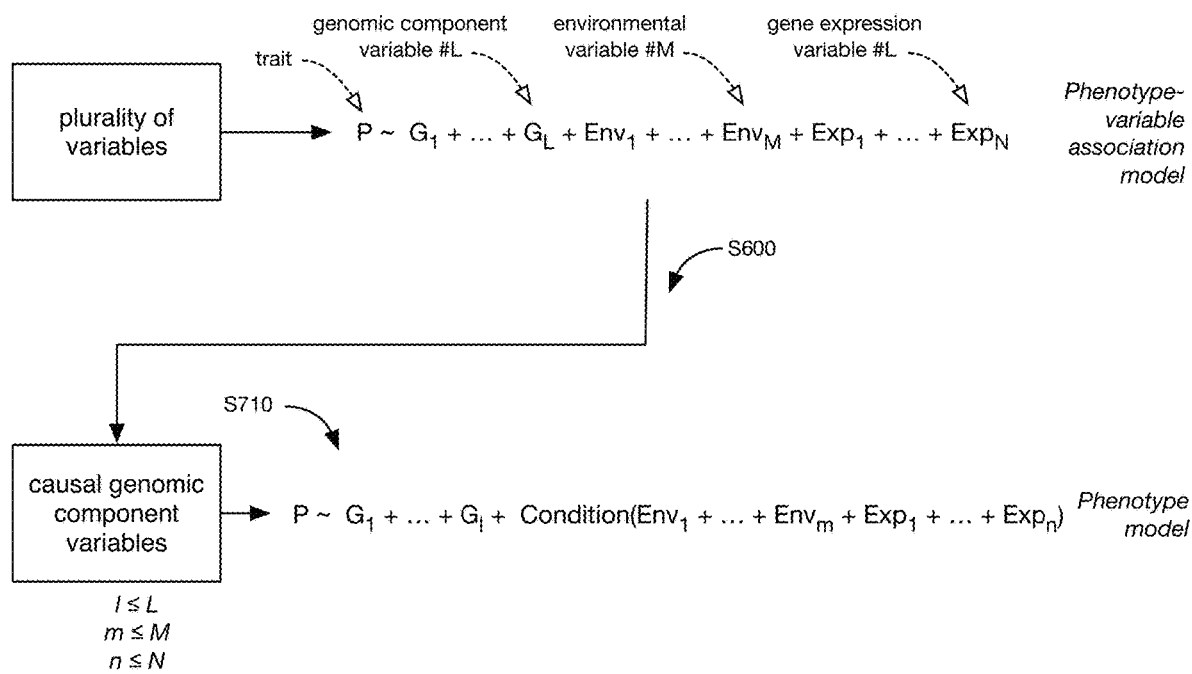
Figure 23C:
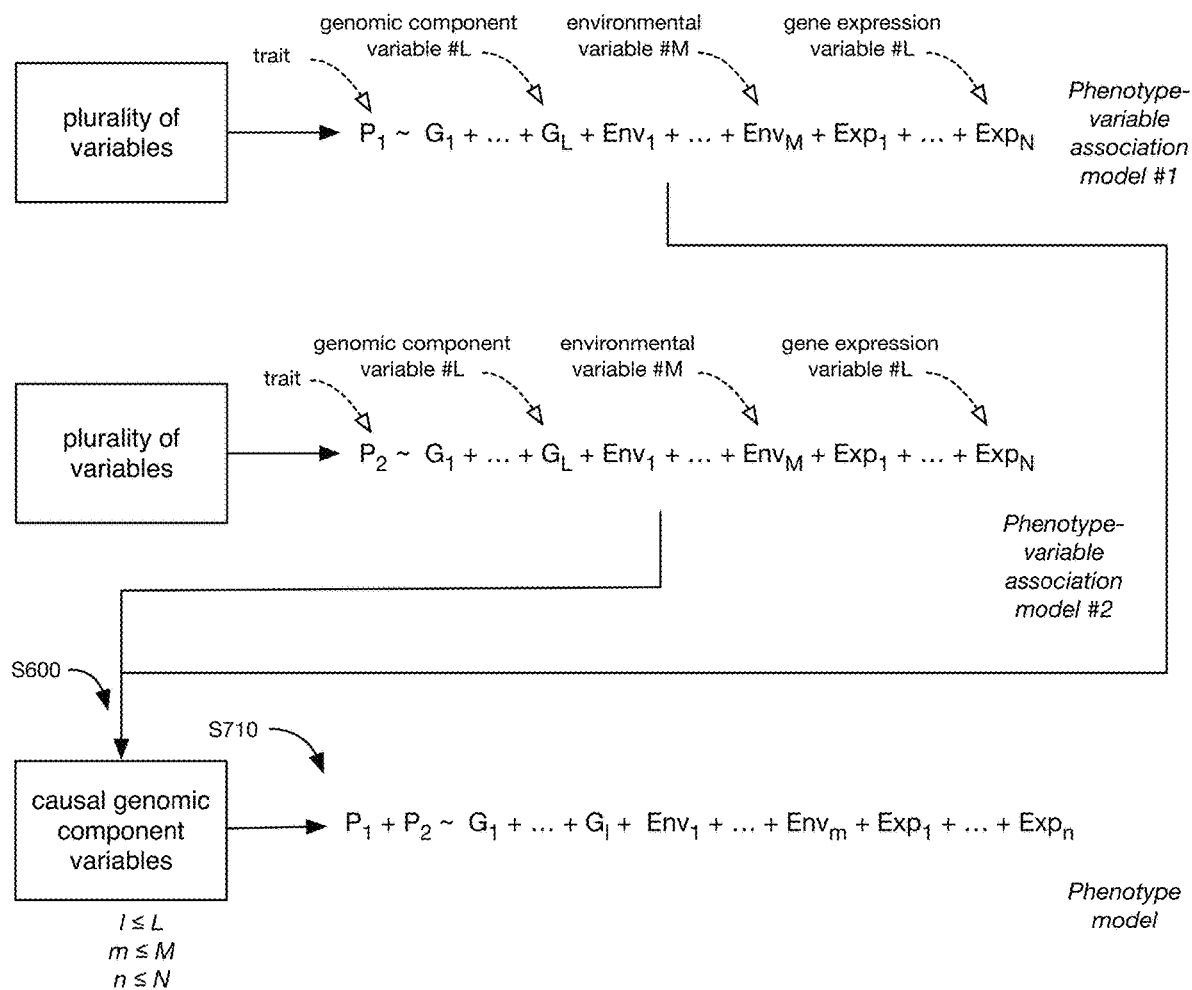

In an illustrative example, a first phenotype and a value for a second phenotype based on values for causal genomic component variables. In a specific example, the causal genomic component variables are a superset of (e.g., include both of) the causal variable sets selected in S600 for the first and second phenotypes. In a third example, the phenotype model predicts a value for a phenotype based on values for causal genomic component variables conditioned on a set of covariates, wherein the set of covariates includes causal environmental variables, causal gene expression variables, causal DNA methylation variables, and/or any other covariates. In a specific example, the phenotype model predicts a value for a phenotype based on values for causal genomic component variables conditioned on a first set of covariates, wherein the conditioned causal genomic component variables are subsequently conditioned on a second set of covariates (e.g., and optionally iteratively conditioned on any number of covariate sets). In a fourth example, the phenotype model predicts a value for a phenotype based on values for causal transcriptome variables, and optionally values for causal genomic component variables, causal environmental variables, and/or causal gene expression variables. Examples are shown in FIG. 23A, FIG. 23B, and FIG. 23C.

However, the phenotype model can be otherwise determined.

Determining a target causal variable value set S730 functions to identify values for the causal variables that will produce a set of target values for the phenotype(s). S730 can be performed after S710, with S750, and/or any other time. S730 or components thereof can be performed: once, iteratively until a stop condition is met (e.g., for a predetermined number of iterations, until a marginal improvement in the predicted phenotype value set falls below a threshold for predetermined number of iterations, until the predicted phenotype value matches the target phenotype value, etc.).

In a first variant, the target causal variable value set is selected from one or more candidate causal variable value sets based on phenotype values predicted by the phenotype model. This variant can include: generating candidate causal variable value sets S731, predicting a phenotype value for each candidate causal variable value set using the phenotype model S733, and/or selecting the target causal variable value set from the candidate causal variable value sets S735. In variants, this can be iteratively performed until the selected causal variable values satisfy a condition (e.g., quality condition, statistical condition, etc.).

Generating the candidate causal variable sets S731 function to create candidate sets of causal variable values. Candidate values for each causal variable can be: predetermined (e.g., manually determined, specified by growing conditions, etc.), randomly determined (e.g., which can avoid local minima), computed (e.g., based on candidate parent variable values, using predictive breeding, using environmental forecasting models, etc.), optimized (e.g., to maximize the predicted trait value, to minimize the predicted trait value, etc.), observed, a combination thereof, and/or otherwise determined. In a first example, candidate causal variable values can be determined for a fixed growing environment, wherein environmental variable values are held constant while other causal variables are permuted (e.g., randomly permuted). In a second example, causal variable values can be selected to optimize a set of causal variables (e.g., to maximize the predicted phenotype value, to minimize the predicted phenotype value, etc.). In a third example, all causal variables are randomly permuted to generate candidate causal variable value sets. In a fourth example, causal variable values can be determined by virtually crossing sets of candidate parent organisms (e.g., with observed and/or known variable values) and determining the values for the causal variables from the one or more virtual children. However, the candidate causal variable values can be otherwise determined.

Predicting a phenotype value for each candidate causal variable value set using the phenotype model S733 can include predicting one or more phenotype values using the phenotype model (determined in S710) given a candidate causal variable value set as input. S733 can be performed for every candidate causal variable value set, a subset of the candidate causal variable value sets (e.g., the most common or most frequently occurring candidate causal variable values sets, a random sample of the candidate causal variable value sets, etc.), and/or for any other suitable set of candidate causal variable values.

S733 can optionally include determining a breeding value for an organism (characterized by a candidate causal variable value set) based on the organism's predicted phenotype values. For example, the breeding value can be determined using: $EBV=b*(P_{individual}-P_{avg})$; where EBV is the estimated breeding value, b is heritability, $P_{individual}$ is the predicted phenotype value for the candidate causal variable value set, and $P_{avg}$ is the average phenotype value (e.g., predicted and/or observed) for a group of causal variable value sets corresponding to an organism population. Heritability can be determined empirically, via breeding simulations, and/or can be otherwise determined. The estimated breeding value is preferably defined such that EBV increases as $P_{individual}$ approaches a target phenotype value set, but alternatively can be otherwise defined.

S733 can optionally include determining a confidence score for the phenotype value prediction. In a first embodiment, the confidence score is determined based on a calculated loss between predicted phenotype values and observed phenotype values (e.g., for a single organism, averaged across organisms in a population, etc.). In a second embodiment, the confidence score is output by the phenotype model itself (e.g., where S710 includes training the model to output the confidence score). However, the confidence score can be otherwise determined.

Selecting the target causal variable value set (TCVVS) from the candidate causal variable value sets (CCVVS) S735 functions to determine which causal variable value set to use (e.g., determine the target organism to breed). The target causal variable value set can be selected based on: predicted phenotype values (e.g., a comparison between predicted and target phenotype values), confidence scores, probability of occurrence (e.g., for a given parent organism set, for a given population, for a given population of parent organisms, etc.), breeding values, breeding parameters (e.g., applying a lower weighting to a candidate causal variable value set that requires more breeding generations lower; applying a lower weighting to a candidate causal variable value set that prescribes more expensive treatments or growing conditions; etc.), a combination thereof, and/or any other information.

Figure 24A:
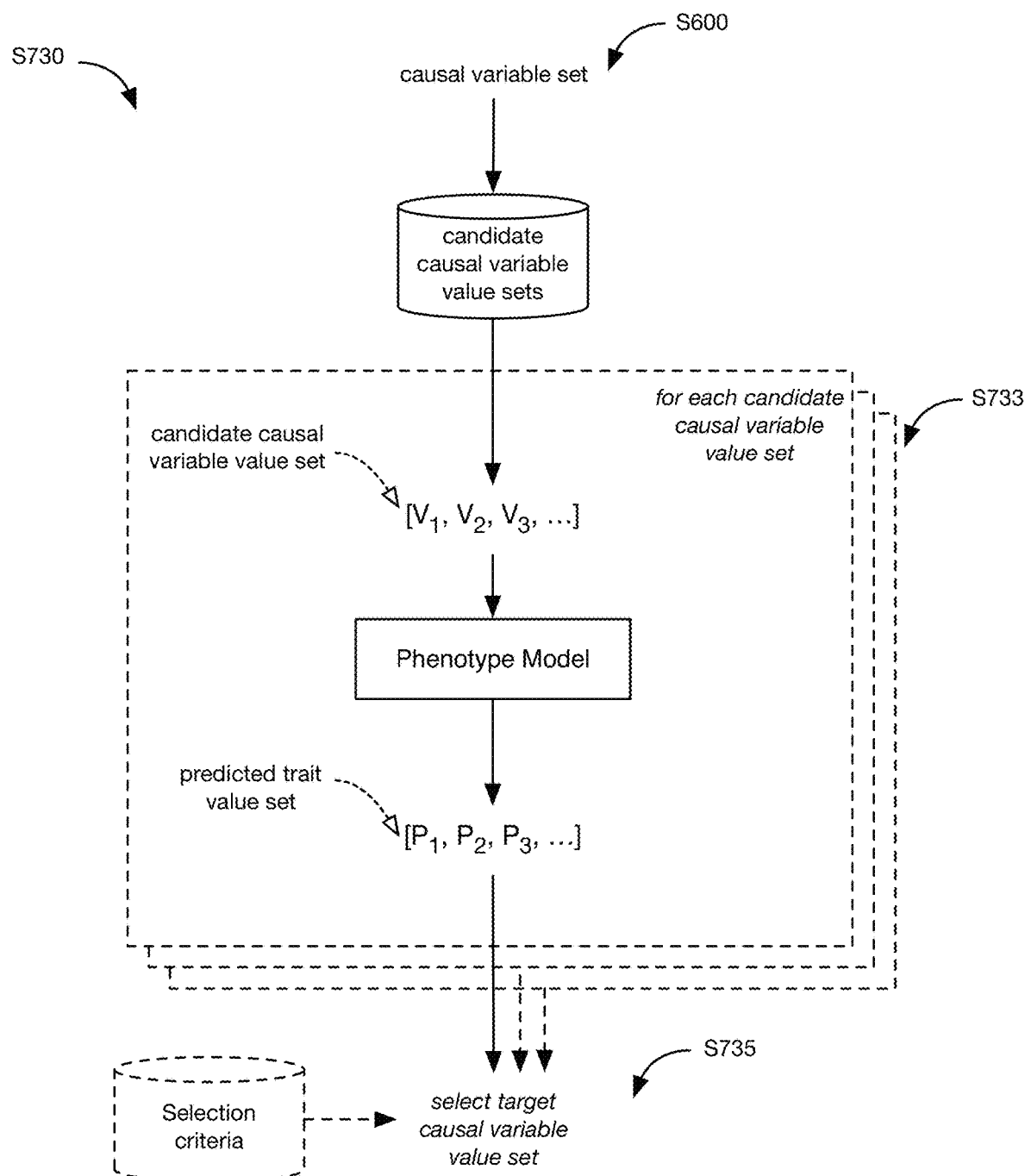
FIG. 24A depicts a first example of determining a target causal variable value set.
Figure 24B:
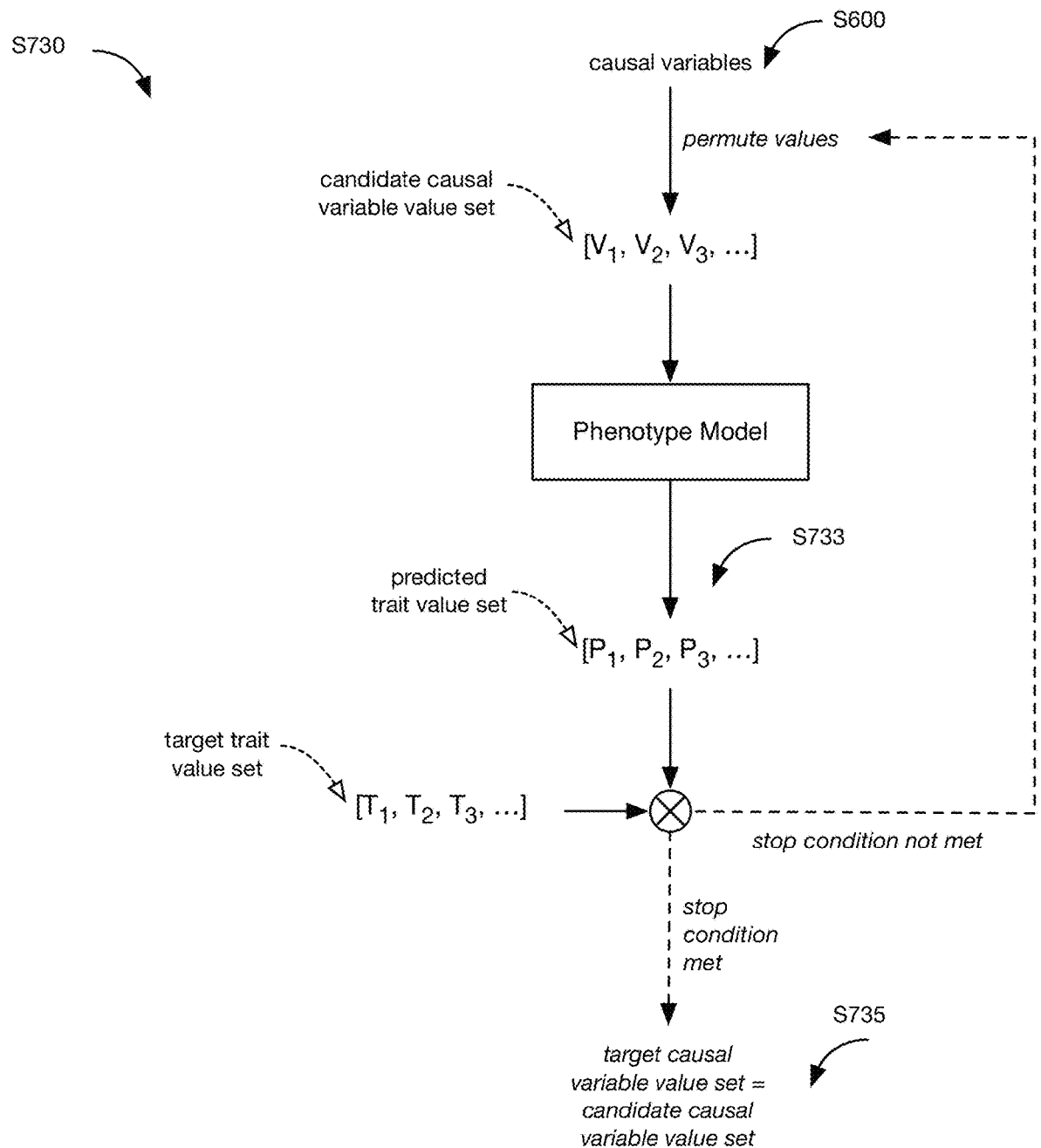
FIG. 24B depicts a second example of determining a target causal variable value set.

In a first example, the CCVVS associated with the most performant phenotype value set is selected as the TCVVS (e.g., example shown in FIG. 24A). The most performant phenotype value set can be the set that matches the exact values in a target phenotype value set, the set with values closest to the values in the target phenotype value set, and/or can be otherwise defined. In a second example, the TCVVS can be selected from the CCVVSs based on the respective predicted phenotype value set and associated confidence score (e.g., where a CCVVS with a low confidence score is less likely to be selected). In a third example, the CCVVS that satisfies a target condition is selected as the TCVVS (e.g., example shown in FIG. 24B). The target condition can be when the predicted phenotype value set is within a threshold of the target phenotype value set, when the estimated breeding value is above a threshold, and/or any other condition. In a fourth example, the TCVVS can be selected based on a distribution. For example, the TCVVS can be selected based on the CCVVS distribution, wherein the TCVVS is the highest-frequency CCVVS, a set of CCVVS within a predetermined number of standard deviations from the mean, and/or otherwise selected based on the CCVVS distribution. In another example, the TCVVS can be selected based on the distribution of phenotype values generated using the CCVVS (e.g., from S733), wherein the CCVVS generating the best combination of phenotype values (e.g., highest days to flower and harvest weight.

In a second variant, the target causal variable value set is determined by optimizing a causal variable value set to minimize loss between the predicted phenotype value set (determined using the updated phenotype-variable association) and the target phenotype value set. For example, the optimization can be performed using one or more causal variable value set seeds, where each seeded causal variable value set can be: observed, randomly determined, and/or be otherwise determined. In a third variant, the target causal variable value set is determined using Bayesian optimization, wherein an acquisition function interrogates the phenotype model to determine the target causal variable value set and/or the parents that could generate the target causal variable value set.

However, the target causal variable value set can be otherwise determined.

Determining breeding parameters to achieve the target causal variable value set S750 functions to determine the set of parent organisms, the environmental conditions, and/or other breeding parameters to breed an organism with the target set of phenotypes. In variants, S750 can determine steps to reach the target causal variable value set and/or target phenotype from an initial causal variable value set. S750 can be performed after S710, after S730 (e.g., based on the target causal variable value set determined in S730), before and/or after any of S100-S600, and/or at any other suitable time. S750 can be iteratively performed, performed once, and/or performed at any other suitable time.

The breeding parameters can include breeding sets (e.g., one or more organisms in the population to cross-breed to achieve the target causal variable value set), a number of breeding generations, treatments (e.g., irradiation, siRNA gene silencing, nutrient application, etc.), growing conditions, and/or any other methods to transform an initial causal variable value set to a target causal variable value set. The breeding parameters preferably exclude genetic engineering (e.g., using CRISPR, foreign gene insertion, etc.), but can alternatively include genetic engineering.

In a first variant, the breeding parameters can be determined using predictive breeding methods. The predictive breeding methods can determine steps to breed one or more organisms—each associated with an observed causal variable value set—to achieve a target organism associated with the target causal variable value set. The one or more organisms can optionally be selected from a larger set of organisms (e.g., existing organisms currently available for breeding; parents). The selected organisms can: have the closest causal variable values to the target causal variable values, have a subset of causal variable values that match the target causal variable values, and/or be otherwise selected.

In a first example, organism sets (e.g., pairs, triplet, quad, etc.) can be selected (e.g., from a set of existing organisms, from a selected set of organisms, etc.) for breeding to achieve genotype values in a target genomic component variable value set.

Figure 25:
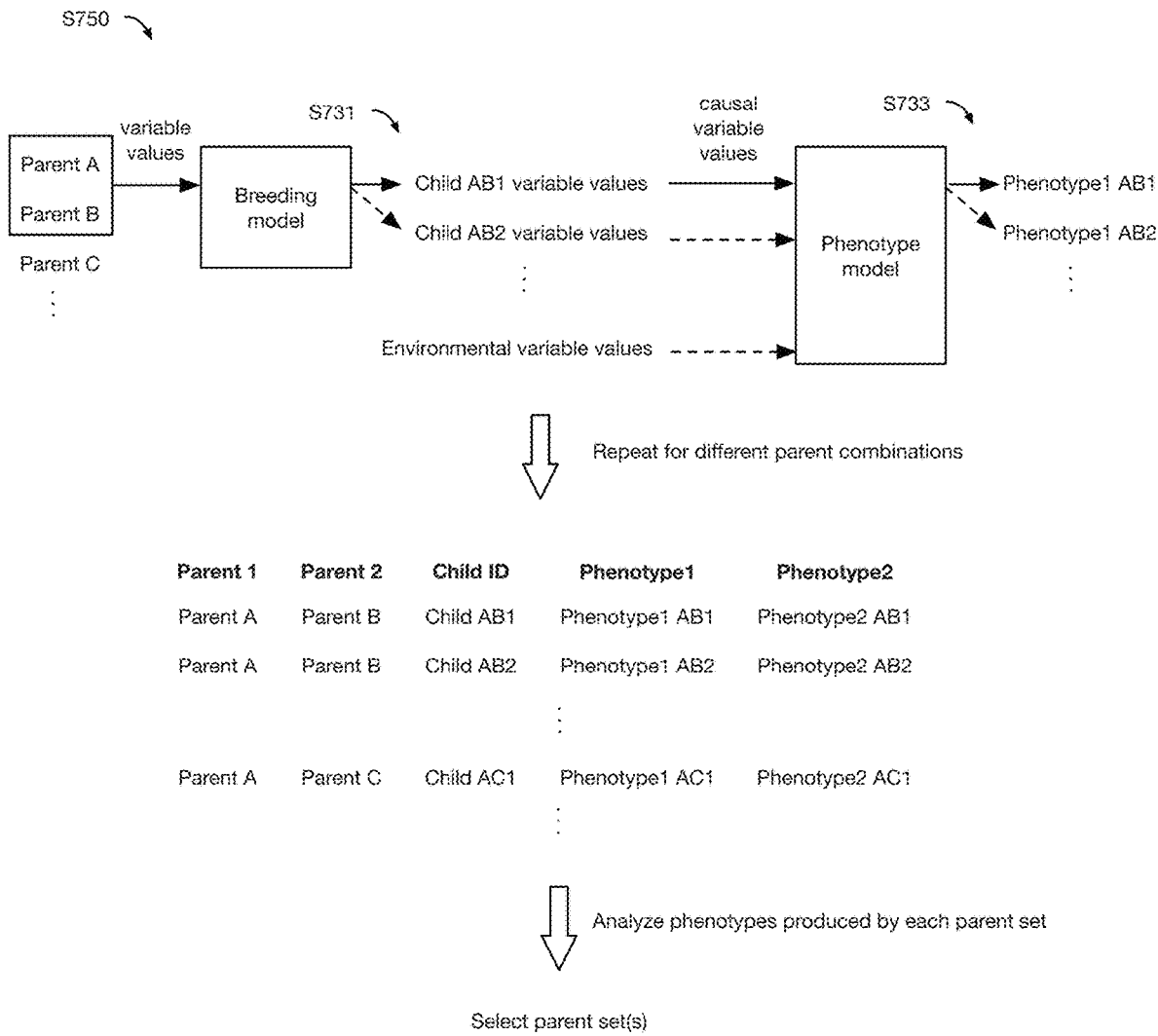
FIG. 25 is a schematic representation of a variant of determining breeding parameters.
Figure 26:
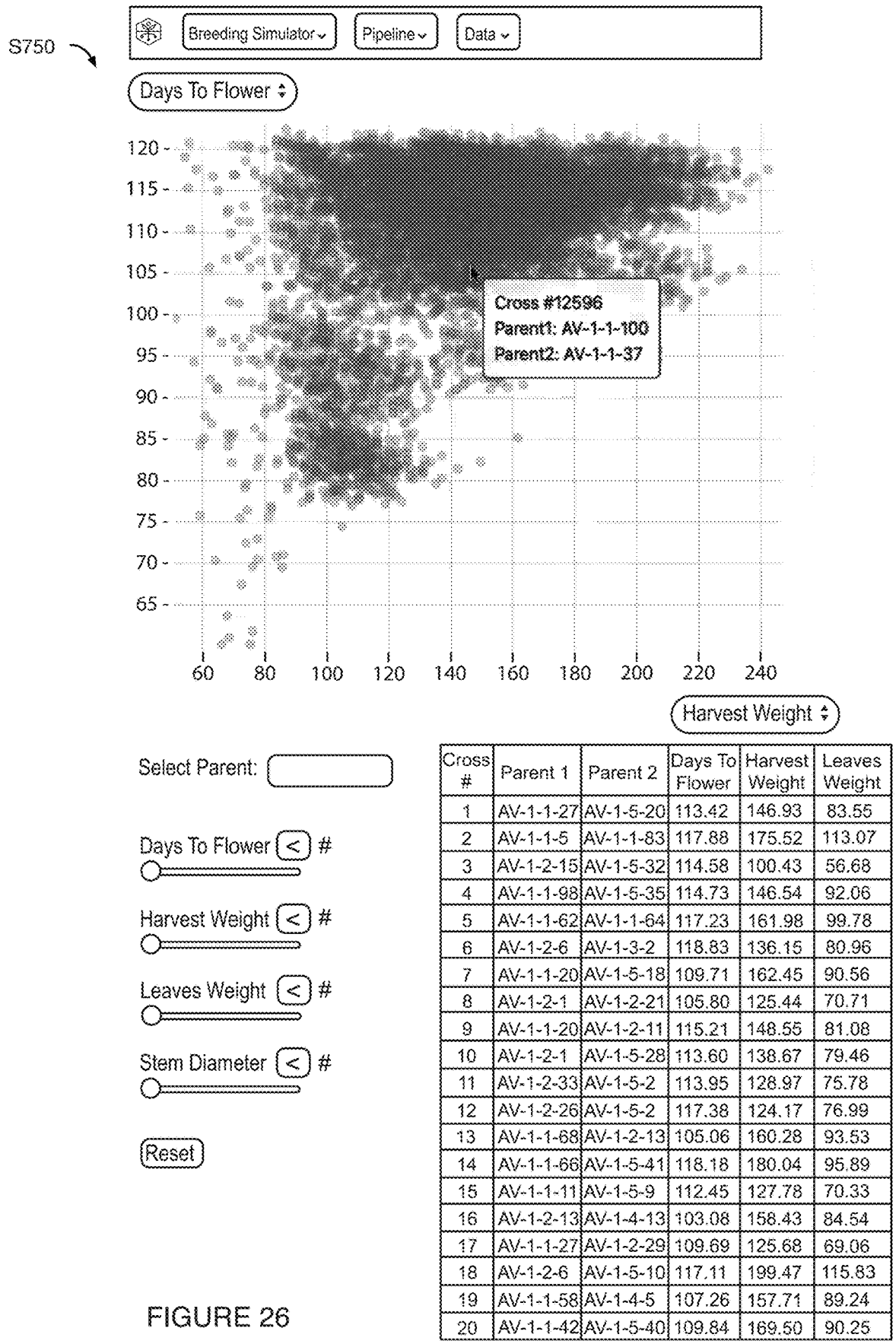
FIG. 26 is an illustrative example of a phenotype value distribution for the descendants of a plurality of parent sets.

In a second example, determining the breeding parameters (e.g., parent organism set) using predictive breeding can include: predicting a set of descendants for each set of parent organisms (e.g., each parent combination); predicting the set of phenotype values for each of the set of descendants (e.g., for each parent organism set); and selecting the parent organism set(s) that produce descendants with phenotype values satisfying a set of conditions (e.g., example shown in FIG. 25 and FIG. 26).

The descendants can include one or more generations. The descendants can be predicted using S731 and/or otherwise determined.

The phenotype values (e.g., traits) can be determined based on the phenotype model and the descendant's causal variable values, be determined using S733, and/or otherwise determined. The phenotype values can be predicted using the same or different phenotype model for different generations. For example, new phenotype models with new causal variables can be determined for different generations (e.g., using one or more of S100-S700), since the causal variables contributing to a phenotype can vary across generations.

The parent organism set can be selected based on the descendants' phenotype values, the distribution of the descendants' phenotype values (e.g., example shown in FIG. 26), and/or otherwise selected. Examples of selection conditions can include selecting the parent sets that: arrive at descendants with the target phenotype values the fastest (e.g., in the least number of generations); produce descendants with the best values (e.g., highest, lowest, etc.) for all or a threshold proportion of phenotypes; produce descendants with the optimal values for all or a threshold proportion of phenotypes; produce descendants with the most and/or least descendants with phenotype values over a set of threshold values (e.g., manually-determined threshold values, the mean phenotype value, median phenotype value, learned phenotype value, etc.); produce descendants with the most and/or least children with phenotype values of a set of threshold values; produce descendants with the most stable phenotype values across generations (e.g., the harvest weight is consistently above a threshold value for the most number of generations and/or more than a threshold number of generations, etc.); produce descendants with the least stable phenotype values across a predetermined number of generations (e.g., the descendants have less-desirable phenotype values after a threshold number of generations); have the highest probability of producing a descendant within a predetermined generation with a set of target phenotype values; the cost to produce the descendants with the target phenotype value(s) (e.g., calculated from the number of generations, the cost to grow each generation, the opportunity cost lost while waiting for the generations to mature, the probability of occurrence, etc.); and/or satisfy any other suitable set of conditions. However, the parent organism set can be selected based on an optimization (e.g., over cost, time, probability of producing a descendant with target phenotype values, etc.), manually selected, automatically selected (e.g., based on satisfaction of one or more of the aforementioned conditions), and/or otherwise determined.

However, the breeding parameters can be otherwise determined based on predictive breeding.

In a second variant, determining breeding parameters includes determining a treatment of an organism (e.g., applied at a given growth stage) that will alter one or more observed variable values to bring an initial causal variable value set closer to the target causal variable value set. The treatment can be determined using known effects of the treatment (e.g., known methylation effects), simulations of treatment at a growth stage, and/or using any other information associated with the treatment and/or the organism. This can be determined in combination with the first variant (e.g., wherein the phenotype values can be determined based on a combination of the variable values from predictive breeding and treatment values) and/or independently from the first variant. The treatment values can be: predicted (e.g., using the phenotype model), manually specified, randomly determined, and/or otherwise determined. In a first example, a treatment of an organism can be determined to increase and/or decrease methylation of one or more genes (e.g., to alter causal DNA methylation variable values, to alter causal genomic expression variable values, etc.). In a second example, a gene therapy can be determined to increase and/or decrease gene expression for one or more genes (e.g., to alter causal genomic expression variable values). In a third example, genetic modification steps can be determined to modify an organism's genome (e.g., to alter causal genomic component variable values). Examples of treatments can include: irradiation, siRNA gene silencing, nutrient application, and/or other treatments. In a fourth example, the environmental parameter values are predetermined and dictated by the growing environment. In a related example, the treatment values can be determined based on other causal variable values (e.g., the genomics of the organism being grown, historic environmental conditions, etc.). In an illustrative example, a treatment amount and frequency (e.g., watering, fertilization, etc.) can be calculated given the phenotype model, the genome of the planted organism (e.g., genomic variable values), the measured environmental conditions (e.g., environmental variable values; soil conditions, nitrogen concentration, etc.), and the desired phenotype value(s). In a fifth example, the treatment parameters can be determined from a user's treatment practice (e.g., a farmer's fertilization schedule). However, the treatment parameters can be otherwise determined.

In a third variant, the breeding parameters include values extracted from the target causal variable value set. In an illustrative example, if the target causal variable value set includes an environmental variable value of 70° F., the temperature to grow the organism in order to achieve this target causal variable value set should be 70° F.

In a fourth variant, the breeding parameters can be determined experimentally. In this variant, the method can include: growing an organism, determining the causal variable values for the organism, predicting the phenotype value based on the causal variable values using the phenotype model, and selecting the organism (and/or the parents of the organism) based on the phenotype value. The organism can be bred using the methods discussed above, randomly bred, and/or otherwise grown. Selecting the organism can include: not killing the organism (e.g., not weeding the organism), treating the organism (e.g., fertilizing the organism, replanting the organism, etc.), and/or otherwise selecting the organism. In variants, this can be performed in real- or near-real time (e.g., while a treatment mechanism is passing over the plant bed) or asynchronously with organism treatment.

However, the breeding parameters can be otherwise determined.

Optionally, a target causal variable value set can be selected (e.g., in S730) based on the breeding parameters. For example, candidate causal variable value sets can be weighted during selection in S735 based on their respective breeding parameters. In an illustrative example, a candidate causal variable value set that requires more breeding generations is weighted lower than a candidate causal variable value set that requires fewer breeding generations. In another illustrative example, a candidate causal variable value set that prescribes more expensive treatments (e.g., more overall nitrogen, more nitrogen applications, etc.) or growing conditions (e.g., a tight temperature range, a tight moisture range, etc.) can be weighted lower than those prescribing less expensive treatments or growing conditions. The method can optionally include breeding organisms in the population based on the breeding parameters to generate a new organism (e.g., with the target phenotype, with the target causal variable value set, etc.).

However, breeding parameters can be otherwise determined.

In an example, the method includes: observing values for a plurality of variables (e.g., genotype, environment, gene expression, DNA methylation, transcriptome, etc.) and observing trait values (e.g., phenotypes) for each organism in a population; generating a first model based on the observed trait values and the observed variable values; and identifying causal variables for a trait from the plurality of variables using the first model. In another example, the method includes: identifying causal variables for a phenotype from the plurality of variables using a phenotype-variable association model; generating a phenotype model relating the causal variables (e.g., only the causal variables) with the phenotype; determining multiple candidate causal variable value sets (e.g., using predictive breeding, by permuting one or more causal variable values); predicting a phenotype value for each candidate causal variable set using the phenotype model; selecting a candidate causal variable value set and/or the associated parent set based on the respective predicted phenotype value; and optionally determining breeding parameter values, such as a series of breeding sets (e.g., breeding pairs), growing conditions, and/or treatments to generate an organism with the selected candidate causal variable value set. In variants, the causal variables can be those having a nonzero (e.g., positive and/or negative) association metric, wherein the association metric can be determined from a difference between an output of the first model (e.g., coefficient, predicted phenotype value, etc.) given observed variable values and an output of the first model given test values for the variable being tested. In variants, the first model can ignore inter-variable interaction effects, while the phenotype model can account for inter-variable interaction effects.

In a first specific example, the goal is to breed an organism that best expresses a phenotype within a given environment. In this example, the environmental variables can be fixed in the phenotype model, and the first model can include or exclude the environmental variables.

In a second specific example, the goal can be to grow an organism that best expresses a phenotype. In this example, the environmental variables can be adjustable, and be accounted for in both the first and phenotype models.

However, S700 can be otherwise performed.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:
1. A method, comprising:
   a) for each of a set of organisms:
      determining a trait value for a trait; and
      determining variable values for a set of variables;
   b) selecting a subset of variables from the set of variables; and
   c) determining a first model configured to predict values for variables of interest in the set of variables based on values for the subset of variables;
   d) determining test variable values for the variables of interest using the first model;
   e) using the test variable values, determining a second model comprising a relationship between the set of variables and the trait;
   f) determining an observed model metric for the second model using variable values for the subset of variables;
   g) determining a test model metric for the second model using the test variable values;
   h) identifying causal variables from the set of variables based on a comparison between the observed model metric and the test model metric;
   i) determining target values for the causal variables based on a target trait; and
   j) based on the target values, breeding organisms in the set of organisms to generate a new organism with the target trait.

2. The method of claim 1, further comprising training the first model using values for a second set of variables, different from the subset of variables.

3. The method of claim 2, wherein the first model comprises an autoencoder.

4. The method of claim 1, wherein determining the first model comprises a fitting a linear regression based on the variable values for the set of variables.

5. The method of claim 1, further comprising clustering the set of variables based on autocorrelation analysis of the variable values, wherein the subset of variables and variables of interest are from a shared cluster.

6. The method of claim 5, wherein variables in the set of variables comprise k-mers.

7. The method of claim 1, wherein (b)-(c) are iteratively repeated until a model fit metric for the first model rises above a threshold.

8. The method of claim 1, wherein a size of the subset of variables is less than a size of the set of organisms.

9. The method of claim 1, further comprising:
   determining a new instance of the first model;

determining new test variable values for the variables of interest using the new instance of the first model; and determining a test model metric based on the new test variable values; wherein the causal variables are further identified based on a comparison between the observed model metric and the new test model metric.

10. The method of claim 1, wherein variables in the set of variables comprise variables for at least one of: loci, gene expression, protein expression, methylation, environmental parameters, or protein binding affinity.

* * * * *